US006569657B1

(12) United States Patent
Meyers et al.

(10) Patent No.: US 6,569,657 B1
(45) Date of Patent: May 27, 2003

(54) 32140, A NOVEL HUMAN ALDEHYDE DEHYDROGENASE AND USES THEREFOR

(75) Inventors: Rachel Meyers, Newton, MA (US); William J. Cook, Natick, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/717,926

(22) Filed: Nov. 21, 2000

Related U.S. Application Data

(60) Provisional application No. 60/214,707, filed on Jun. 27, 2000.

(51) Int. Cl.[7] .............................. C12N 9/04; C12N 1/20; C12N 15/00; C12P 21/04; C07H 21/04
(52) U.S. Cl. ................... 435/190; 435/71.1; 435/252.3; 435/325; 435/320.1; 536/23.2
(58) Field of Search ............................ 435/190, 252.3, 435/325, 320.1, 71.1; 536/23.2

(56) References Cited

U.S. PATENT DOCUMENTS 6,136,599 A * 10/2000 Cho ........................... 435/325

OTHER PUBLICATIONS

Cook et al. Isolation and characterization of cDNA clones for rat liver 10–formyltetrahydrofolate dehydrogenase. J. Biol. Chem. 266 (8), 4965–4973 (1991).*
Cook, R. J., et al., "Isolation and Characterization of cDNA Clones for Rat Liver 10–Formyltetrahydrofolate Dehydrogenase," *The Journal of Biological Chemistry*, Mar. 15, 1991, pp. 1965–1973, vol. 266, No. 8.

Hong, M. et al., "Isolation and Characterization of cDNA Clone for Human Liver 10–Formyltetrahydrofolate Dehydrogenase," *Biochemistry and Molecular Biology International*, Mar. 1999, pp. 407–415, vol. 47, No. 3.

Yoshida, A., et al., "Human Aldehyde Dehydrogenase Gene Family," *European Journal of Biochemistry*, Feb. 1998, pp. 549–557, vol. 251, No. 3.

EMBL Database Report for Accession No. AA424371, 1997 (Unpublished (XP–002212692).

EMBL Database Report for Accession No. AF052732, Sep. 21, 1998 (XP–002212693).

EMBL Database Report for Accession No. M59861, May 1, 1991 (XP–002212694).

* cited by examiner

Primary Examiner—Ponnathapu Achutamurthy
Assistant Examiner—Yong Pak
(74) Attorney, Agent, or Firm—Alston & Bird LLP

(57) ABSTRACT

The invention provides isolated nucleic acids molecules, designated 32140 nucleic acid molecules, which encode novel aldehyde dehydrogenase family members. The invention also provides antisense nucleic acid molecules, recombinant expression vectors containing 32140 nucleic acid molecules, host cells into which the expression vectors have been introduced, and nonhuman transgenic animals in which a 32140 gene has been introduced or disrupted. The invention still further provides isolated 32140 proteins, fusion proteins, antigenic peptides and anti-32140 antibodies. Diagnostic methods utilizing compositions of the invention are also provided.

31 Claims, 12 Drawing Sheets

```
Input file Fbh32140FL1.seq; Output File 32140.trans
Sequence length 7220

AGCGGCGAGCCGCGAACCAGGCAGTCCGGGGCATCCAGACTGCAGGCCGCGCCCAGGCCGCGCCCAGGCTGCGCCGCCC

M   L   R   R   G   S   Q      7
GCCTGCCTCCCGCGCTGCCGCGTCGCCAGTGCTAGCGCTCCTCTCCAGC ATG CTG CGG CGG GGC AGC CAG     21
  A   L   R   R   F   S   T   G   R   V   Y   F   K   N   K   L   K   L   A   L     27
GCG CTC CGG CGC TTC TCC ACT GGC CGG GTT TAT TTC AAA AAC AAG CTG AAG TTG GCA CTA    81
  I   G   Q   S   L   F   G   Q   E   V   Y   S   H   L   R   K   E   G   H   R     47
ATT GGC CAG AGC CTC TTT GGA CAA GAA GTC TAT AGC CAC CTC CGC AAA GAG GGC CAC CGA   141
  V   V   G   V   F   T   V   P   D   K   D   G   K   A   D   P   L   A   L   A     67
GTA GTA GGG GTG TTC ACA GTT CCA GAC AAG GAT GGA AAA GCT GAC CCT CTG GCT TTG GCT   201
  A   E   K   D   G   T   P   V   F   K   L   P   K   W   R   V   K   G   K   T     87
GCA GAG AAA GAT GGG ACC CCT GTG TTC AAG CTT CCT AAA TGG AGG GTC AAG GGC AAG ACC   261
  I   K   E   V   A   E   A   Y   R   S   V   G   A   E   L   N   V   L   P   F    107
ATC AAA GAA GTG GCA GAA GCC TAC AGA TCC GTG GGT GCA GAG CTA AAT GTG CTC CCT TTC   321
  C   T   Q   F   I   P   M   D   I   I   D   S   P   K   H   G   S   I   I   Y    127
TGC ACT CAG TTC ATT CCC ATG GAT ATA ATT GAT AGT CCA AAG CAC GGC TCT ATC ATT TAT   381
  H   P   S   I   L   P   R   H   R   G   A   S   A   I   N   W   T   L   I   M    147
CAC CCA TCC ATC CTG CCC AGG CAC AGA GGA GCC TCT GCT ATC AAT TGG ACT CTA ATT ATG   441
  G   D   K   K   A   G   F   S   V   F   W   A   D   D   G   L   D   T   G   P    167
GGA GAT AAG AAA GCT GGG TTT TCT GTT TTC TGG GCT GAT GAT GGC TTG GAT ACA GGA CCC   501
  I   L   L   Q   R   S   C   D   V   E   P   N   D   T   V   D   A   L   Y   N    187
ATC CTT CTT CAG AGA TCA TGT GAT GTT GAA CCC AAT GAT ACA GTG GAT GCA CTT TAT AAT   561
  R   F   L   F   P   E   G   I   K   A   M   V   E   A   V   Q   L   I   A   D    207
CGG TTT CTT TTT CCT GAA GGA ATC AAG GCC ATG GTA GAA GCT GTC CAA CTC ATA GCT GAT   621
  G   K   A   P   R   I   P   Q   P   E   E   G   A   T   Y   E   G   I   Q   K    227
GGA AAA GCT CCT CGT ATA CCC CAG CCA GAA GAA GGG GCA ACA TAT GAA GGT ATC CAG AAA   681
  K   E   N   A   E   I   S   W   D   Q   S   A   E   V   L   H   N   W   I   R    247
AAG GAA AAT GCT GAG ATT TCT TGG GAC CAG TCT GCC GAA GTT TTA CAT AAC TGG ATT CGA   741
  G   H   D   K   V   P   G   A   W   T   E   I   N   G   Q   M   V   T   F   Y    267
GGT CAT GAT AAA GTC CCT GGA GCT TGG ACA GAG ATA AAT GGA CAG ATG GTC ACT TTC TAT   801
  G   S   T   L   L   N   S   S   V   P   P   G   E   P   L   E   I   K   G   A    287
GGC TCG ACA TTA CTG AAT AGC TCT GTG CCT CCT GGA GAA CCA CTG GAA ATT AAA GGT GCC   861
  K   K   P   G   L   V   T   K   N   G   L   V   L   F   G   N   D   G   K   A    307
AAG AAG CCT GGT CTC GTT ACC AAA AAT GGA CTT GTT CTT TTT GGT AAC GAT GGA AAA GCA   921
  L   T   V   R   N   L   Q   F   E   D   G   K   M   I   P   A   S   Q   Y   F    327
CTG ACG GTG AGA AAT CTG CAG TTT GAA GAT GGA AAA ATG ATC CCT GCC TCT CAG TAC TTT   981
```

FIG. 1A

```
  S   T   G   E   T   S   V   V   E   L   T   A   E   E   V   K   V   A   E   T   347
TCA ACG GGT GAG ACG TCA GTG GTA GAA CTG ACA GCT GAA GAG GTG AAA GTG GCA GAG ACC 1041
  I   K   V   I   W   A   G   I   L   S   N   V   P   I   I   E   D   S   T   D   367
ATC AAG GTC ATC TGG GCT GGA ATT TTA AGC AAT GTC CCC ATT ATT GAA GAC TCA ACA GAC 1101
  F   F   K   S   G   A   S   S   M   D   V   A   R   L   V   E   E   I   R   Q   387
TTC TTT AAA TCT GGA GCA AGC TCA ATG GAT GTT GCC AGG CTG GTT GAA GAG ATC AGA CAG 1161
  K   C   G   G   L   Q   L   Q   N   E   D   V   Y   M   A   T   K   F   E   G   407
AAA TGT GGT GGG CTT CAG TTG CAG AAT GAA GAT GTC TAT ATG GCC ACC AAG TTT GAA GGC 1221
  F   I   Q   K   V   V   R   K   L   R   G   E   D   Q   E   V   E   L   V   V   427
TTT ATC CAA AAG GTC GTG AGG AAA CTG AGA GGA GAA GAT CAA GAG GTG GAG CTG GTT GTA 1281
  D   Y   I   S   K   E   V   N   E   I   M   V   K   M   P   Y   Q   C   F   I   447
GAT TAT ATT TCA AAG GAG GTC AAT GAA ATC ATG GTA AAA ATG CCA TAC CAG TGT TTC ATA 1341
  N   G   Q   F   T   D   A   D   D   G   K   T   Y   D   T   I   N   P   T   D   467
AAT GGA CAG TTC ACA GAT GCA GAC GAT GGA AAG ACT TAC GAC ACT ATC AAC CCA ACA GAT 1401
  G   S   T   I   C   K   V   S   Y   A   S   L   A   D   V   D   K   A   V   A   487
GGA TCT ACA ATA TGC AAA GTA TCC TAC GCT TCT TTG GCG GAT GTT GAT AAA GCA GTA GCA 1461
  A   A   K   D   A   F   E   N   G   E   W   G   R   M   N   A   R   E   R   G   507
GCA GCA AAA GAT GCT TTT GAA AAC GGT GAA TGG GGA AGA ATG AAT GCA AGA GAA AGA GGA 1521
  R   L   M   Y   R   L   A   D   L   L   E   E   N   Q   E   E   L   A   T   I   527
AGA TTG ATG TAT AGA CTT GCA GAC CTA CTG GAA GAG AAC CAA GAA GAG CTG GCA ACT ATT 1581
  E   A   L   D   S   G   A   V   Y   T   L   A   L   K   T   H   I   G   M   S   547
GAA GCC CTT GAT TCA GGG GCT GTC TAT ACC TTG GCC CTG AAG ACA CAC ATT GGA ATG TCT 1641
  V   Q   T   F   R   Y   F   A   G   W   C   D   K   I   Q   G   S   T   I   P   567
GTG CAA ACA TTC AGA TAT TTT GCT GGC TGG TGC GAC AAA ATT CAG GGT TCT ACT ATT CCA 1701
  I   N   Q   A   R   P   N   R   N   L   T   F   T   K   K   E   P   L   G   V   587
ATC AAC CAG GCC CGT CCA AAT CGC AAT CTG ACC TTC ACC AAG AAA GAG CCA CTC GGT GTC 1761
  C   A   I   I   I   P   W   N   Y   P   L   M   M   L   A   W   K   S   A   A   607
TGT GCC ATT ATT ATT CCC TGG AAC TAC CCG CTG ATG ATG CTG GCA TGG AAG AGT GCT GCG 1821
  C   L   A   A   G   N   T   L   V   L   K   P   A   Q   V   T   P   L   T   A   627
TGT TTG GCA GCA GGC AAT ACC TTA GTG CTC AAG CCA GCA CAG GTC ACG CCC TTG ACT GCT 1881
  L   K   F   A   E   L   S   V   K   A   G   F   P   K   G   V   I   N   I   I   647
TTG AAG TTT GCA GAA CTG TCT GTG AAA GCA GGC TTT CCA AAG GGG GTC ATC AAC ATC ATT 1941
  P   G   S   G   G   I   A   G   Q   R   L   S   E   H   P   D   I   R   K   L   667
CCA GGC TCA GGT GGC ATA GCA GGA CAA CGT CTG TCT GAA CAT CCT GAC ATC CGC AAA CTT 2001
  G   F   T   G   S   T   P   I   G   K   Q   I   M   K   S   C   A   V   S   N   687
GGT TTC ACT GGA TCC ACT CCT ATT GGC AAA CAG ATC ATG AAG AGC TGT GCT GTT AGC AAC 2061
  L   K   K   V   S   L   E   L   G   G   K   S   P   L   I   I   F   N   D   C   707
TTG AAG AAA GTT TCC CTT GAG CTT GGT GGC AAG TCT CCA CTT ATA ATA TTT AAT GAC TGT 2121
```

FIG. 1B

```
  E   L   D   K   A   V   R   M   G   M   G   A   V   F   F   N   K   G   E   N    727
 GAA CTT GAC AAG GCT GTG CGA ATG GGC ATG GGA GCA GTA TTT TTC AAC AAA GGA GAG AAC   2181
  C   I   A   A   G   R   L   F   V   E   E   S   I   H   D   E   F   V   T   R    747
 TGT ATT GCT GCT GGG CGG TTG TTC GTG GAA GAA TCC ATC CAC GAC GAA TTT GTG ACA AGA   2241
  V   V   E   E   I   K   K   M   K   I   G   D   P   L   D   R   S   T   D   H    767
 GTG GTA GAA GAA ATT AAA AAG ATG AAA ATT GGT GAT CCA CTT GAC AGA TCC ACT GAT CAT   2301
  G   P   Q   N   H   K   A   H   L   E   K   L   L   Q   Y   C   E   T   G   V    787
 GGG CCC CAA AAT CAT AAG GCT CAT CTG GAA AAG CTG CTG CAA TAC TGT GAA ACT GGA GTG   2361
  K   E   G   A   T   L   V   Y   G   G   R   Q   V   Q   R   P   G   F   F   M    807
 AAA GAA GGG GCC ACT TTG GTG TAC GGG GGA AGA CAA GTC CAA AGG CCA GGC TTT TTC ATG   2421
  E   P   T   V   F   T   D   V   E   D   Y   M   Y   L   A   K   E   E   S   F    827
 GAG CCG ACC GTG TTC ACA GAT GTG GAA GAC TAC ATG TAC CTC GCC AAA GAG GAA TCC TTT   2481
  G   P   I   M   V   I   S   K   F   Q   N   G   D   I   D   G   V   L   Q   R    847
 GGG CCT ATT ATG GTC ATT TCT AAA TTC CAA AAT GGG GAC ATC GAT GGA GTG TTG CAG CGA   2541
  A   N   S   T   E   Y   G   L   A   S   G   V   F   T   R   D   I   N   K   A    867
 GCA AAT AGT ACA GAG TAT GGT TTG GCC TCA GGG GTT TTT ACA AGA GAC ATA AAC AAA GCT   2601
  M   Y   V   S   E   K   L   E   A   G   T   V   F   I   N   T   Y   N   K   T    887
 ATG TAT GTG AGT GAA AAA CTG GAA GCA GGA ACT GTT TTT ATT AAC ACA TAC AAC AAG ACA   2661
  D   V   A   A   P   F   G   G   V   K   Q   S   G   F   G   K   D   L   G   E    907
 GAT GTG GCG GCC CCA TTT GGC GGA GTT AAA CAA TCT GGC TTT GGA AAA GAC TTA GGT GAG   2721
  E   A   L   N   E   Y   L   K   T   K   T   V   T   L   E   Y   *                924
 GAA GCT CTA AAT GAA TAT CTC AAA ACC AAG ACG GTG ACA CTG GAA TAT TAG              2772
```

AGCAACACCATCATCAGGAAAGCCTTGACAGACAGCCCTTTACAACTCTGGACACACTTAAGAAGATTGGGTGTGTTGA
GGCAGGAGGTGTCAGCCACAAACCAAAAAATACACAGATGGACCATGAAGAGGGCCAGGCCATGTTAAAGCATTTACAC
ATGTGCCTGAGTATTTTCTAATACACCTTCCAGTGATTTGGAGTTGTTGCATTTTGACTATGTTGTATATCATACGTAT
TTCTAAAATACCAAGCTGTTTCTCCCCTACCTAGACAAATCTATTCATGGTTCCCATCTTGAAGATGTCAGTACCATGC
AGTTATAATACACAAGGTGCATTTATTGGAAACTTTGTATAATATGTACAGGTTTTTAACCTCTGAACTATACATAGGG
GGTTATTAAAAAGATTTTCTATAAGTCTTCTAAGGAACAGTATAACCTGTAAGGAATGTGAAGGTAGTTCTTTTTTAGT
ATTTGGAAATAAGATACATCTTTGTGCCTTTGATATTCCATTTTTTAACCCACTGTGATGGGTGATCAACCTAGAAACA
TTATCTTGAGTACCTACTAGGTACCAGGTACTATATTATGTTCTGAGGAGTATAGAGAATTTAATGATATGATGGCTGG
CCCCCACATAGTTTAAATTTTAGTAAATAGCTTTGAAGCAAATTTTACATATGATATAGTAGAAGGCTGATCCCTGGT
CGTATCATACCATCTTCCTATCTATGTAACTTGGGAAACTCTCGCAACTCCTCTGAGCCTCTGCTTCCCTATGTGTAA
AACAGGGATAGTAAATGCCTTCCTCAGGACCCTAATAGGAGAATTCATTGCAGTAATGTAAGTAAAGCACCTCACATT
AATGCTTTGCTCATGGTAAGTACTCAAATTTAACTCTGATTTCCTCCGTCACCATTCTTAAAAGATATTGAGATAGTTT
AATTAACTAGATGAATTCATTTCCCACAACCCTTTTCAATCATCAATTCCTAGATATTTTTCTCATCCATTGTTCTGAC

FIG. 1C

ACAATGCCTGATACAGCAGCACTGAAAAATGCCACACAATGAAAAATGGCAATAGTACAAGGAAAAGGGGTGCTTTTCT
TTGGGCAGCTCGCTCGTCCTTCATGGGACATCTTACTTTCCATTTTTCTACCTATTGGTTCTGCTGTTCACTGGCTGTG
TGATCTTGGGCAAGATAGTAATCTAATATCTCAGAGCCTAGGTTGAGTATCTATAAAATGAAAATCAAATCTCTATCTC
AGTAGGTGTTGCAAGGATTCAGTGAGATAATATACATAATGCACTTAACAAGGCGTTTGGACCATAGCATTGAAGAAAT
GGAAACTATTAACAGCCCATTTCCCATTGGCAGACAGAAGTAGTCAGGTGAGTAAATTTTCACCATCTATGTGTGACTA
GAAGGCGGCAAATTTCTGAATCACATGAGTCTCCAAAAGATAGCCAGAAAGTTAAATTCTATTAATCCTCCTTTAAAAA
TAAAATTTCAGTAAACATTCCTTTTTCTTTGGCTTTGAAGAAGCCTTAGGGAATATTTGTCATTTTGGAGACTTGGCAG
AATAACATGAGGGGATTGTAGGGAATCAATAAAAACTAAACAACAAAATCAGAGTCAGAGAACATTTTCAAAAGGAAGA
ATAGGAGGTTTGATCCCAGCATGATAAACAGAGCGAATTTGGCCTGGAAGCACTTTTGATTATACTATAGCTCATTTAC
CATCCCAGAGTTTGGCACAGCTGAAATTTTAAGTTGGAATGAATATTCACTGGGCCCAAAATGACAGTTCATATTTGAA
TAAAAGTGACAAAAGCCTTTTTATAAGTAATCACTTTTAAGTGAAATGTTTTAACTGATTTCATGTGATTTAGAATATG
ATTTAATCAAATTATTTTAATGATAGATGGAATGGCAGACAAAAACATGCCTGTCCTTCTAGACTGATTTTACTTTACC
CTCTAATATTCATCTCAGTAGCAGTGTTTTAAATATTCTCTGGGCTGCAAAACTCTTTGGGAATCTGATAAAAGCTATG
AACACTCCCTGTGTCCCGCTTCTACCCCCAAAATTCATGTGCACACACACAATTCTGCAAGTATCTTCAAAGGGTTCAC
AGACCTCCCAAAGGCCATGCTTGGGCCCCAGATTAAGAACTCCTTTCTCCATAGCAAGTTTTAAACATTTCTTACCAGC
TTACATTTTTAGATCTGGCTGATCAGAATCAAAGGCTCTGTGTAATACATAAAGTTACCAAGTGAACTGGAATTGGAAC
ATCACCCTCCCCAGCCTGCTAGGTGATTTACTTAACACATAGAGTAATAAAATCATCGCTGTTGCTTTAGATCACGGAT
TATTTTGCTAATAATGCTAAGGATGAAGCTGTGATCTTATTATCACCTGAATCGGGAGGTGTGGACACTTTAAGCAGTT
CCACTTTCCTTCTAATTCCCCATCCCCATGCCTTTGCTAAAGCTGTCCCTTTTGCTCTAACACCCTTCCTGGACCTTCC
TACCCTAGCTGGGCTAAGTGTTTCTCCTCAGCGTTCCCACTTGTTTCAAACATAGCACTTACCACTTGTACTAAAATTA
CTTGCCTTCTTAATTAGATATGAACAACCCTCCCCAACTCCAGTATGGGCCTTCTGTCAATAATAATACGATATGACAG
CTACCATTTATTAAGGGCCTCCTGTATGAAAGACCTTAGGCTAAGCATGTTTTAAATGTTATTTAATCTTCACAATCTC
TGAAAAAAATGAAGAAATCAACGTGCTTTTCTTACTACCTCTACCCCTAAGCCATTATTACTTTTTTTTTTTTTTGAG
ACAGAGTTTTGCTCTTGTTGCCCAGGCTGCAGTGCAGTGGTGCAATCTTGGCTCACTGCAACCTCTGCCTCTTGGGTTC
AAGCGATTGTCATGCCTTAGCCTTCCAAGTAGCTGGGATTACAGGTGTGTGCCACTACACCTGGCTAAGTAGAGATGGG
GTTTCGCCATGTTGGCCAGGCTGGTCTTGAACTCCTGACCTCAAGTGATCCACCTGCCTCCGCCTCCCAAAGTGCTGGG
ATTACAGGCATGAACCACTGCACCTGGCCTGTTACCTCTTTCCTACAATTTTGCTCAAGTCTCCCAACTGGTCTTCTGG
ATTCCTCTCTTCTGCGGTCCTGTTCAAAGCTTAAGTCAGACAGTGTCACTTCACTCGTCTGTTTAAAACCTTTCAATGG

FIG. 1D

CCCCCATTTCACGTAGACCAAAGTCCAACGTATTTACCTGGCCTACTGATCTTGCTCCTAGCTACCTCTGACCTCATCT

CCTGTCAATTTCCCTCTCATTCTGTTCCACCATCCTGACTGCCTTGACTTCCTCAACAGAACAAGCCTGCTCCTGCCTC

AGGGCCTCTGTCCTTATTCTTCCTCTTCCCAGGGGTGTGCTGGTAAAATATTTAACAAATAGTTCTCCGGGACGGGGGA

GAAAACCCTCATTTGTAGCATTTGCAGGTATCTATGTGTAAATACTCTCATCAAGGCTATTTTTGAGCCACTAATTTGC

CTTCACTGAATACAGAGTTTGGGAAGAGATGCATGCCATCAGAACAAATGCAAGCCAGCACCAGCACACCACTGCCTCT

TCCTGCAACTCTTGTCCATACACAACCTCATGGCTGGCTGGCTCACTTCCTGCAGGTCTCTCCTCAAATATCATCTGAT

GAGAGACACATTCCCTGACTATGCTTTCTAAAATAGGCCATATGCCCCCACATTCATACCCCATCTGCTGTCATTCTTT

ATTCTTTTTATAAGTGCATTATTTTCATAGCACTTATCACTACCTGTTGTATATTAATCAATGATCTTTTCCCATTAGA

ATGTAAGTTTCATGAACAGGTACTTGTTTTAATACTGTATCTCCAGTCCTAATGTGTAACAGGAGCCCAATAAATGTTT

GCTTTCAAATGGAGAGGTTAAGTAACCTGCTCAAATCACACAGCTATTAAGTGGCAGAACAGGTTTTCAAGCAATGCAT

CTGGTGGTTTTAACTAAGTCGAGATAGTTTTTATTCCTAATGCCTAAATCAGGGCCTAGGTAGTGAGCTGTGGGCACAT

ATTAAGTATTGGTTAAACTAAAAATAATAAGCAAAATGGACATTATCTATAAAAGCTTTTGTGGAAATGGCTAGAGCTA

GGGTAAGGAAACAAATTTGGTTCCCCATACCTGCCCTTCAAGAAAATAAAGCTGTCAAGGAAAATTGGGCTAAGAGTAG

GATATGAGGGATGATGGATAAGGCATGAGACATGAGAAAATAAGGGGGATTAAA

FIG. 1E

```
aldedh: domain 1 of 1, from 450 to 923: score 821.3, E = 3.4e-243
                 *->ewvdsasgktfevvNPankgevigrvpeataeDvdaAVkAAkeAfks
                    +++d+  gkt++++NP + g++i+ v+ a+ +Dvd+AV+AAk Af++
       32140  450  QFTDADDGKTYDTINPTD-GSTICKVSYASLADVDKAVAAAKDAFEN 495

GpwWakvpaseRariLrkladlieeredeLaaletlDlGKplaeAkgDte
                   G +W+++ a+eR+r++++ladl+ee+++eLa +e+lD G  + A++ t+
       32140  496  G-EWGRMNARERGRLMYRLADLLEENQEELATIEALDSGAVYTLALK-TH 543 vgraideiryyagwarklmgerrvipslatdgde.elnytrrePlGVvgv
                   +g+ ++ +ry+agw++k+ g     +++++  +++++l++t++ePlGV+++
       32140  544  IGMSVQTFRYFAGWCDKIQG---STIPINQARPNrNLTFTKKEPLGVCAI 590

IsPWNFPlllalwklapALAaGNTVVlKPSEqTPltalllaelieeaGan
                   I+PWN+Pl++++wk a++LAaGNT VlKP++ TPltal++ael  +aG
       32140  591  IIPWNYPLMMLAWKSAACLAAGNTLVLKPAQVTPLTALKFAELSVKAG-- 638 nlPkGVvnvvpGfGaevGqaLlshpdidkisFTGSteVGklimeaAAakn
                   +PkGV+n++pG+G+  +Gq L++hpdi+k+ FTGSt++Gk+im+++A +n
       32140  639  -FPKGVINIIPGSGGIAGQRLSEHPDIRKLGFTGSTPIGKQIMKSCAVSN 687 lkkVtLELGGKsPvIVfdDADLdkAverivfgaFgnaGQvCiApsRllVh
                   lkkV+LELGGKsP I+f+D+ LdkAv++ ++++F+n G++CiA+ Rl+V+
       32140  688  LKKVSLELGGKSPLIIFNDCELDKAVRMGMGAVFFNKGENCIAAGRLFVE 737 esiydeFveklkervkklkliGdpldsdtniyGPlIseqqfdrvlsyIed
                   esi+deFv +++e++kk+k iGdpld+ t + GP+ ++++++++l+y+e
       32140  738  ESIHDEFVTRVVEEIKKMK-IGDPLDRSTDH-GPQNHKAHLEKLLQYCET 785 gkeeGAkvlcGGerdeskeylggGyyvqPTiftdVtpdMkImkEEIFGPV
                   g++eGA++++GG+++ ++      G++ +PT+ftdV + M  +kEE FGP+
       32140  786  GVKEGATLVYGGRQVQRP-----GFFMEPTVFTDVEDYMYLAKEESFGPI 830 lpiikfkd..ldEAIelaNdteYGLAayvFTkdilarafrvakaleaGiV
                   ++i kf ++++d ++++aN+teYGLAa++vFT+d +++a++v+++leaG+V
       32140  831  MVISKFQNGdIDGVLQRANSTEYGLASGVFTRD-INKAMYVSEKLEAGTV 879 wvNDvcvhaaepqlPFGGvKqSSGiGrehgGkygleeYteiKtVtirl<-
                   ++N  +++ +++ +PFGGvKq SG+G+++ G+ +l+eY+ +KtVt+++
       32140  880  FIN--TYNKTDVAAPFGGVKQ-SGFGKDL-GEEALNEYLKTKTVTLEY   923
                      *

FIG. 7B

| Lung/ COPD | Spleen/ normal | Tonsil/ normal | Lymph node/ normal | Thymus/ normal | Epithelial Cells | Endothelial Cells | Skeletal Muscle | Fibroblasts (Dorm) | Skin/ normal | Adipose/ Normal | Osteoblasts (prima) | Osteoblasts (Undiff) | Osteoblasts (Diff) | Osteoclasts | Aortic SMC Early | Aortic SMC Late | shear HUVEC | static HUVEC | Osteoclasts (Undiff) |
|---|---|---|---|---|---|---|---|---|---|---|---|---|---|---|---|---|---|---|---|
| 40.00 | 40.00 | 40.00 | 40.00 | 40.00 | 30.57 | 40.00 | 40.00 | 36.16 | 40.00 | 40.00 | 34.93 | 34.49 | 33.29 | 40.00 | 26.80 | 30.41 | 40.00 | 40.00 | 40.00 |
| 18.60 | 20.41 | 18.50 | 19.18 | 20.08 | 21.01 | 21.18 | 20.96 | 19.53 | 21.53 | 19.44 | 20.59 | 19.54 | 18.61 | 18.10 | 20.77 | 23.53 | 20.90 | 21.38 | 17.40 |
| 21.40 | 19.59 | 21.50 | 20.83 | 19.93 | 9.56 | 18.82 | 19.06 | 15.63 | 18.47 | 20.57 | 14.34 | 14.96 | 14.69 | 21.90 | 6.03 | 6.88 | 19.10 | 18.62 | 22.60 |
| 0.00 | 0.00 | 0.00 | 0.00 | 0.00 | 1.32 | 0.00 | 0.00 | 0.00 | 0.00 | 0.00 | 0.05 | 0.03 | 0.04 | 0.00 | 15.30 | 8.49 | 0.00 | 0.00 | 0.00 |

FROM FIG. 7A.

… 
32140, A NOVEL HUMAN ALDEHYDE DEHYDROGENASE AND USES THEREFOR

CROSS-REFERENCE TO RELATED APPLICATION

This application claims the benefit of U.S. Provisional Application No. 60/214,707, filed Jun. 27, 2000.

FIELD OF THE INVENTION

The invention relates to novel aldehyde dehydrogenase-like sequences and proteins. Also provided are vectors, host cells, and recombinant methods for making and using the novel molecules.

BACKGROUND OF THE INVENTION

Aldehydes are a class of highly-reactive molecules that are involved in a number of biological processes. The biological effects mediated by some aldehydes are beneficial, but other members of this class of molecule are associated with biological toxicity, mutagenesis, and carcinogenesis. Aldehydes are generated from a large number of endogenous and exogenous sources. The metabolism of amino acids, lipids, steroids, vitamins, and some amines leads to the formation of aldehydes, and they can also be derived from a number of drugs and environmental agents (reviewed by Lindahl, (1992) Crit. Rev. Biochem. Mol. Biol. 27:283–335).

The aldehyde dehydrogenases make up a large family of enzymes that oxidize aldehydes to their less-reactive carboxylic acids. The members of this family of $NAD^+$ (nicotinamide adenine dinucleotide)- or NADP (nicotinamide adenine dinucleotide phosphate)-dependent enzymes share structural and functional features and generally exhibit broad substrate specificity, catalyzing the oxidation of both aliphatic and aromatic aldehydes (reviewed by Lindahl, supra). The aldehyde dehydrogenase family includes both cytoplasmic and mitochondrial members. Various members of the mammalian family of aldehyde dehydrogenase are expressed in liver, stomach, lung, kidney, testis, salivary gland, muscle, heart, and brain (reviewed by Yoshida et al., (1998) Eur. J. Biochem. 251:549–557).

Aldehyde dehydrogenases are also involved in a number of key metabolic pathways, including, but not limited to, the metabolism of arginine, proline, glutamate, glycine, serine, threonine, histidine, tyrosine, tryptophan, ascorbate, aldarate, β-alanine, butanoate, fatty acids, glycerolipids, pyruvate, propanoate, 4-aminobutyric acid (GABA), retinoic acid, and xenobiotics; the degradation of lysine, valine, leucine, and isoleucine; and the biosynthesis of bile acids. In addition, mutations in members of the human aldehyde dehydrogenase have been associated with a number of diseases including Sjögren-Larsson syndrome, alcohol flushing syndrome, and type II hyperprolinemia (reviewed by Vasiliou et al., (1999) Pharmacogenetics 9: 421–434). Changes in aldehyde dehydrogenase activity have also been associated with a number of cancers, including liver, urinary bladder, colon, and mammary cancers (reviewed by Lindahl, (1992) Crit. Rev. Biochem. Mol. Biol. 27:283–335).

The critical role that aldehyde dehydrogenases play in numerous biological processes and diseases make them important targets for therapeutic intervention. It is consequently important to identify novel genes coding for members of this enzyme family.

SUMMARY OF THE INVENTION

The present invention is based, in part, on the discovery of a novel human aldehyde dehydrogenase, referred to herein as "32140". The nucleotide sequence of a cDNA encoding 32140 is shown in SEQ ID NO:1, and the amino acid sequence of a 32140 polypeptide is shown in SEQ ID NO:2. In addition, the nucleotide sequence of the coding region is depicted in SEQ ID NO:3.

Accordingly, in one aspect, the invention features a nucleic acid molecule which encodes a 32140 protein or polypeptide, e.g., a biologically active portion of the 32140 protein. In a preferred embodiment, the isolated nucleic acid molecule encodes a polypeptide having the amino acid sequence of SEQ ID NO:2. In other embodiments, the invention provides an isolated 32140 nucleic acid molecule having the nucleotide sequence shown in SEQ ID NO:1, SEQ ID NO:3, or the sequence of the DNA insert of the plasmid deposited with ATCC as Accession Number PTA-3424. In still other embodiments, the invention provides nucleic acid molecules that are substantially identical (e.g., naturally occurring allelic variants) to the nucleotide sequence shown in SEQ ID NO: 1, SEQ ID NO:3, or the sequence of the DNA insert of the plasmid deposited with ATCC as Accession Number PTA-3424. In other embodiments, the invention provides a nucleic acid molecule which hybridizes under stringent hybridization conditions to a nucleic acid molecule comprising the nucleotide sequence of SEQ ID NO:1, SEQ ID NO:3, or the sequence of the DNA insert of the plasmid deposited with ATCC as Accession Number PTA-3424, wherein the nucleic acid encodes a full length 32140 protein or an active fragment thereof.

In a related aspect, the invention further provides nucleic acid constructs, which include a 32140 nucleic acid molecule described herein. In certain embodiments, the nucleic acid molecules of the invention are operatively linked to native or heterologous regulatory sequences. Also included are vectors and host cells containing the 32140 nucleic acid molecules of the invention e.g., vectors and host cells suitable for producing 32140 nucleic acid molecules and polypeptides.

In another related aspect, the invention provides nucleic acid fragments suitable as primers or hybridization probes for the detection of 32140-encoding nucleic acids.

In still another related aspect, isolated nucleic acid molecules that are antisense to a 32140 encoding nucleic acid molecule are provided.

In another aspect, the invention features 32140 polypeptides, and biologically active or antigenic fragments thereof that are useful, e.g., as reagents or targets in assays applicable to treatment and diagnosis of 32140-mediated or -related disorders. In another embodiment, the invention provides 32140 polypeptides having a 32140 activity. Preferred polypeptides are 32140 proteins including at least one aldehyde dehydrogenase domain, and, preferably, having a 32140 activity, e.g., a 32140 activity as described herein.

In other embodiments, the invention provides 32140 polypeptides, e.g., a 32140 polypeptide having the amino acid sequence shown in SEQ ID NO:2; the amino acid sequence encoded by the cDNA insert of the plasmid deposited with ATCC as Accession Number PTA-3424; an amino acid sequence that is substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1, SEQ ID NO:3, or the sequence of the DNA insert of the plasmid deposited with ATCC as Accession Number PTA-3424, wherein the nucleic acid encodes a full length 32140 protein or an active fragment thereof.

In a related aspect, the invention further provides nucleic acid constructs which include a 32140 nucleic acid molecule described herein.

In a related aspect, the invention provides 32140 polypeptides or fragments operatively linked to non-32140 polypeptides to form fusion proteins.

In another aspect, the invention features antibodies and antigen-binding fragments thereof, that react with, or more preferably specifically bind 32140 polypeptides.

In another aspect, the invention provides methods of screening for compounds that modulate the expression or activity of the 32140 polypeptides or nucleic acids.

In still another aspect, the invention provides a process for modulating 32140 polypeptide or nucleic acid expression or activity, e.g. using the screened compounds. In certain embodiments, the methods involve treatment of conditions related to aberrant activity or expression of the 32140 polypeptides or nucleic acids, such as conditions involving aberrant or deficient cellular proliferation or differentiation.

More particularly, 32140 is associated with viral disease. It is induced in Herpes Simplex Virus (HSV)-infected human ganglia and neuroblastoma. It was observed to be induced up to 5-fold in HSV-infected neuroblastoma cells. It is hypothesized that HSV induces expression of a novel 10-formyltetrahydrofolate DH isozyme encoded by gene 32140, particularly in infected neurons.

The invention also provides assays for determining the activity of or the presence or absence of 32140 polypeptides or nucleic acid molecules in a biological sample, including assays for the diagnosis of disease. Gene 32140 showed expression in the following tissues, including but not limited to: brain, spinal cord, heart, mammary gland, salivary gland, small intestine, stomach, testis, uterus, and trachea.

In further aspect the invention provides assays for determining the presence or absence of a genetic alteration in a 32140 polypeptide or nucleic acid molecule, including assays for the diagnosis of disease.

BRIEF DESCRIPTION OF THE DRAWINGS

FIGS. 1A–1E depicts a cDNA sequence (SEQ ID NO:1) and predicted amino acid sequence (SEQ ID NO:2) of human 32140. The methionine-initiated open reading frame of human 32140 (without the 5' and 3' untranslated regions) extends from nucleotide position 129 to position 2897 of SEQ ID NO:1, not including the terminal codon (coding sequence shown in SEQ ID NO:3).

FIG. 3 depicts an alignment of the aldehyde dehydrogenase domain of human 32140 with a consensus amino acid sequence derived from a hidden Markov model (HMM; alignment determined using the hmmpfam algorithm of the HMMer version 2 software package, described herein). The upper sequence is the consensus amino acid sequence (SEQ ID NO:4), while the lower amino acid sequence corresponds to amino acids 450 to 923 of SEQ ID NO:2.

FIG. 7 shows Phase 1.2.2 Expression of Gene 32140/33767 w/β2 in a pathology screening panel where gene 32140 expression is assayed in normal and diseased tissue. Diseased human tissues include tumor and fibrotic tissues.

Figure 2:
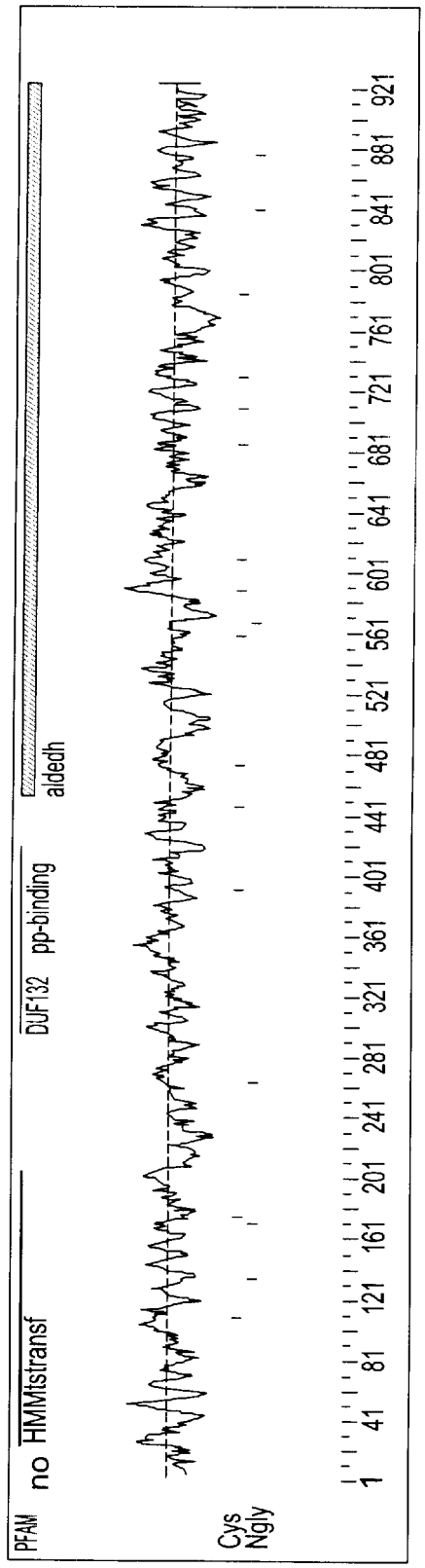
FIG. 2 depicts a hydropathy plot of human 32140. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence of human 32140 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or as N-glycosylation site.

Other features and advantages of the invention will be apparent from the following detailed description, and from the claims.

DETAILED DESCRIPTION OF THE INVENTION

Human 32140

The human 32140 sequence (FIGS. 1A–E; SEQ ID NO:1), which is approximately 7220 nucleotides long including untranslated regions, contains a predicted methionine-initiated coding sequence of about 2769 nucleotides (nucleotides 129–2897 of SEQ ID NO:1; SEQ ID NO:3), not including the terminal codon. The coding sequence encodes a 923 amino acid protein (SEQ ID NO:2).

Human 32140 contains the following regions: a predicted aldehyde dehydrogenase domain (PFAM Accession PF00171) located at about amino acid residues 450–923 of SEQ ID NO:2, and a predicted formyl transferase (PFAM Accession PF00551) located at about amino acid residues 23–202 of SEQ ID NO:2.

The 32140 protein also includes the following domains: 10-formyltetrahydrofolate dehydrogenase (at about amino acid residues 265–336 of SEQ ID NO:2), and formyltransferase/methyltransferase (at about amino acid residues 211–328 of SEQ ID NO:2).

For general information regarding PFAM identifiers, PS prefix and PF prefix domain identification numbers, refer to Sonnhammer et al. (1997) *Protein* 28:405–420 and the web site http//www.psc.edu/general/software/packages/pfam/pfam.html.

A plasmid containing the nucleotide sequence encoding human 32140 was deposited with American Type Culture Collection (ATCC), 10801 University Boulevard, Manassas, Va. 20110-2209, on Jun. 1, 2001 and assigned Accession Number PTA-3424. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C §112.

The 32140 protein contains a significant number of structural characteristics in common with members of the aldehyde dehydrogenase family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "aldehyde dehydrogenase" refers to a protein or polypeptide which is capable of catalyzing an aldehyde oxidation reaction. Aldehyde dehydrogenases can have a specificity for various aldehyde precursors. An aldehyde dehydrogenase polypeptide typically includes a region of sequence similarity that comprises both the $NAD^+$/NADP binding site and the enzyme active site (Vasiliou et al., (1999) *Pharmacogenetics* 9:421–434). This region of sequence similarity is located at about amino acids 669–728 of SEQ ID NO:2. The 32140 polypeptide exhibits sequence identity with the aldehyde dehydrogenase family at four key amino acid residues that have been shown to be important for aldehyde dehydrogenase function, including a glutamate involved in catalytic activity (amino acid 694 of SEQ ID NO:2), a cysteine involved in substrate binding (amino acid 728 of SEQ ID NO:2), and two glycines involved in $NAD^+$ or NADP binding (amino acids 671 and 676 of SEQ ID NO:2).

Typically, aldehyde dehydrogenases play a role in a wide variety of cellular processes. For example, the metabolism of many amino acids, fatty acids, and glycerolipids, as well as ascorbate, aldarate, butanoate, pyruvate, propanoate, and 4-aminobutyric acid. (GABA), involves specific oxidation reactions catalyzed by aldehyde dehydrogenases. Aldehyde dehydrogenases also participate in retinoid signaling, catalyzing the oxidation of retinal (which is required for vision) to retinoic acid (which plays an important role as a signaling molecule in embryonic differentiation) (reviewed by Duester, in *Enzymology and Molecular Biology of Carbonyl Metabolism*, Keuwer Academic/Plenum Publishers,1989). Thus, the molecules of the present invention may be involved in one or more of: 1) the oxidation of an aldehyde; 2) the modulation of amino acid metabolism; 3) the modulation of fatty acid or glycerophospholipid metabolism; 4) the modulation of retinoic acid signaling; 5) the modulation of cell differentiation; 6) the modulation of vision; 7) the modulation of 4-aminobutyric acid (GABA) metabolism; 8) the modulation of the metabolism of drugs or environmental agents; 9) the modulation of alcohol metabolism;10) the modulation of tumor cell growth and invasion; or 11) the modulation of vitamin metabolism.

A 32140 polypeptide can include an "aldehyde dehydrogenase domain" or regions homologous with an "aldehyde dehydrogenase domain". As used herein, the term "aldehyde dehydrogenase domain" includes an amino acid sequence of about 80–300 amino acid residues in length and having a bit score for the alignment of the sequence to the aldehyde dehydrogenase domain (HMM) of at least 8. Preferably, an aldehyde dehydrogenase domain includes at least about 100–250 amino acids, more preferably about 130–200 amino acid residues, or about 160–200 amino acids and has a bit score for the alignment of the sequence to the aldehyde dehydrogenase domain (HMM) of at least 16 or greater. The aldehyde dehydrogenase domain (HMM) has been assigned the PFAM Accession PFOO171 (http://pfam.wustl.edu/). An alignment of the aldehyde dehydrogenase domain (amino acids 450–923 of SEQ ID NO:2) of human 32140 with a consensus amino acid sequence derived from a hidden Markov model is depicted in FIG. 3.

In a preferred embodiment, 32140 polypeptide or protein has a "aldehyde dehydrogenase domain" or a region which includes at least about 100–250 more preferably about 130–200 or 160–200 amino acid residues and has at least about 60%, 70%, 80%, 90%, 95%, 99%, or 100% homology with an "aldehyde dehydrogenase domain," e.g., the aldehyde dehydrogenase domain of human 32140 (e.g., amino acid residues 450–923 of SEQ ID NO:2).

To identify the presence of an "aldehyde dehydrogenase" domain in a 32140 protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al., (1997) *Proteins* 28(3):405–420 and a detailed description of HMMs can be found, for example, in Gribskov et al., (1990) *Meth. Enzymol.* 183:146–159; Gribskov et al., (1987) *Proc. Natl. Acad. Sci. USA* 84:4355–4358; Krogh et al., (1994) *J. Mol. Biol.* 235:1501–1531; and Stultz et al., (1993) *Protein Sci.* 2:305–314, the contents of which are incorporated herein by reference.

As the 32140 polypeptides of the invention may modulate 32140-mediated activities, they may be useful for developing novel diagnostic and therapeutic agents for 32140-mediated or related disorders, as described below.

As used herein, a "32140 activity", "biological activity of 32140" or "functional activity of 32140", refers to an activity exerted by a 32140 protein, polypeptide or nucleic acid molecule on e.g., a 32140-responsive cell or on a 32140 substrate, e.g., a lipid or protein substrate, as determined in vivo or in vitro. In one embodiment, a 32140 activity is a direct activity, such as an association with a 32140 target molecule. A "target molecule" or "binding partner" is a molecule with which a 32140 protein binds or interacts in nature, e.g., an aldehyde, which the 32140 protein oxidizes. A 32140 activity can also be an indirect activity, e.g., a cellular signaling activity mediated by interaction of the 32140 protein with a 32140 ligand. For example, the 32140 proteins of the present invention can have one or more of the following activities: 1) the oxidation of an aldehyde; 2) the modulation of amino acid metabolism; 3) the modulation of fatty acid or glycerophospholipid metabolism; 4) the modulation of retionic acid signaling; 5) the modulation of cell differentiation; 6) the modulation of vision; 7) the modulation of 4-aminobutyric acid (GABA) metabolism; 8) the modulation of the metabolism of drugs or environmental agents; 9) the modulation of alcohol metabolism; 10) the modulation of tumor cell growth and invasion; or 11) the modulation of vitamin metabolism. 12) the ability to antagonize or inhibit, competitively or non-competitively, any of 1–11.

Accordingly, 32140 protein may mediate various disorders, including cellular proliferative and/or differentiative disorders, lung disorders, liver disorders, brain disorders, heart disorders, kidney disorders, breast disorders, and testis disorders.

Examples of cellular proliferative and/or differentiative disorders include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

The terms "cancer" or "neoplasms" include malignancies of the various organ systems, such as affecting lung, breast, thyroid, lymphoid, gastrointestinal, an genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix,. lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

The 32140 nucleic acid and protein of the invention can be used to treat and/or diagnose a variety of proliferative disorders. E.g., such disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L., (1991) *Crit. Rev. in Oncol./Hemotol.* 11:267–97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lynphomas, adult T cell leukemia/lymphoma (ATL), cutaneous T-cell lymphoma (CTCL), large granular lymphocytic leukemia (LGF), Hodgkin's disease and Reed-Stemberg disease.

Figure 4:
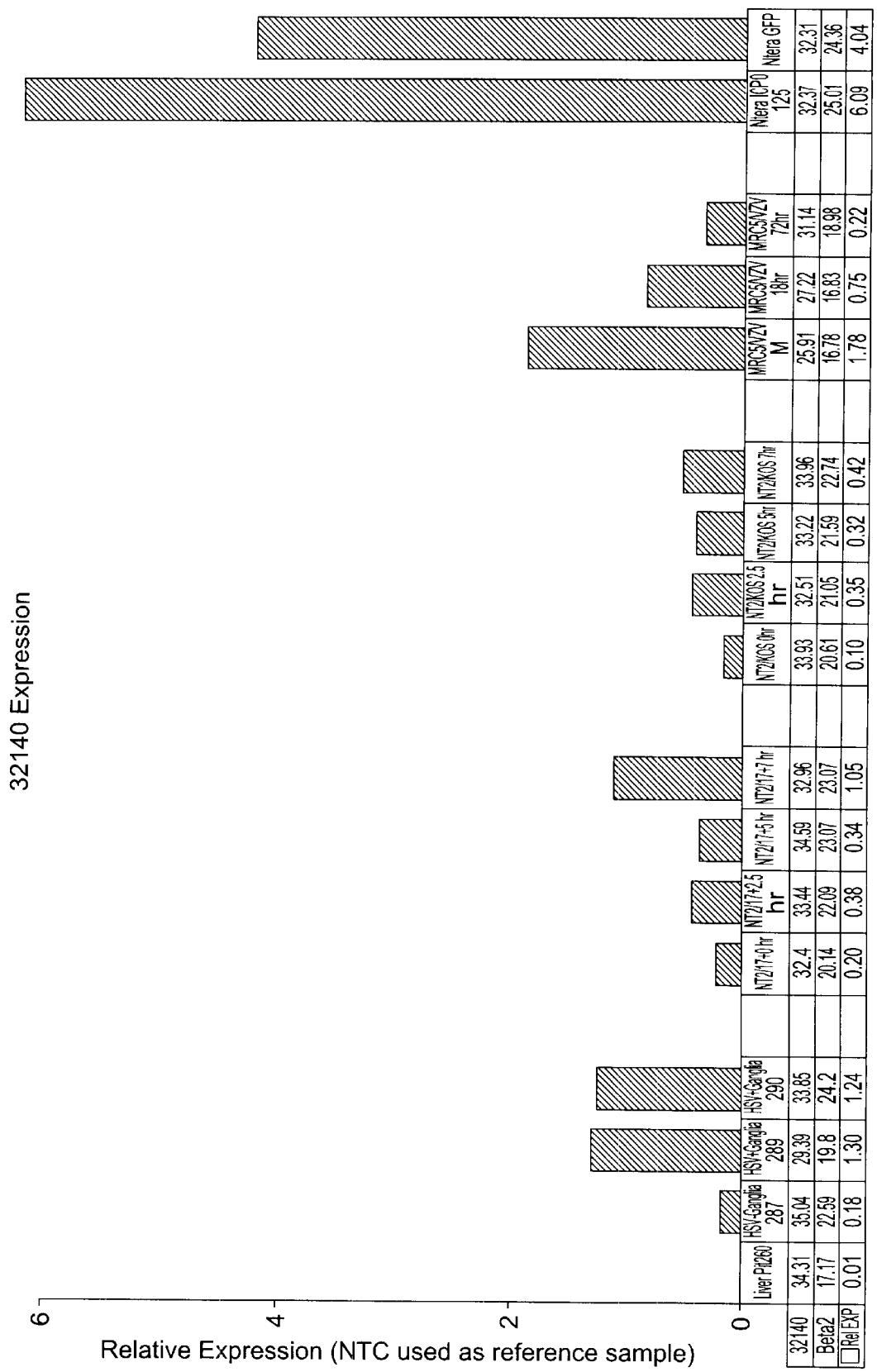
FIG. 4 shows gene 32140 expression in different cells. Left to right: 32140 expression in normal or uninfected liver; next 3 panels show expression in uninfected ganglia (287) and ganglia infected with Herpes Simplex Virus (289 and 290); next 4 panels are samples from a time course of HSV (strain 17+) infection of human Ntera2 neuroblastoma cells (times are 0, 2.5, 5, and 7 hours post-infection); next 4 panels are for same infection experiment using HSV strain KOS; next 3 panels are for a time course of Varicella Zoster virus (VZV) infected human MRC5 (lung fibroblast cells) (times are 0, 18 and 72 hours post-infection); last 2 panels are Ntera2 cells infected with an adenovirus that expresses the HSV ICPO transcription factor.
Figure 5:
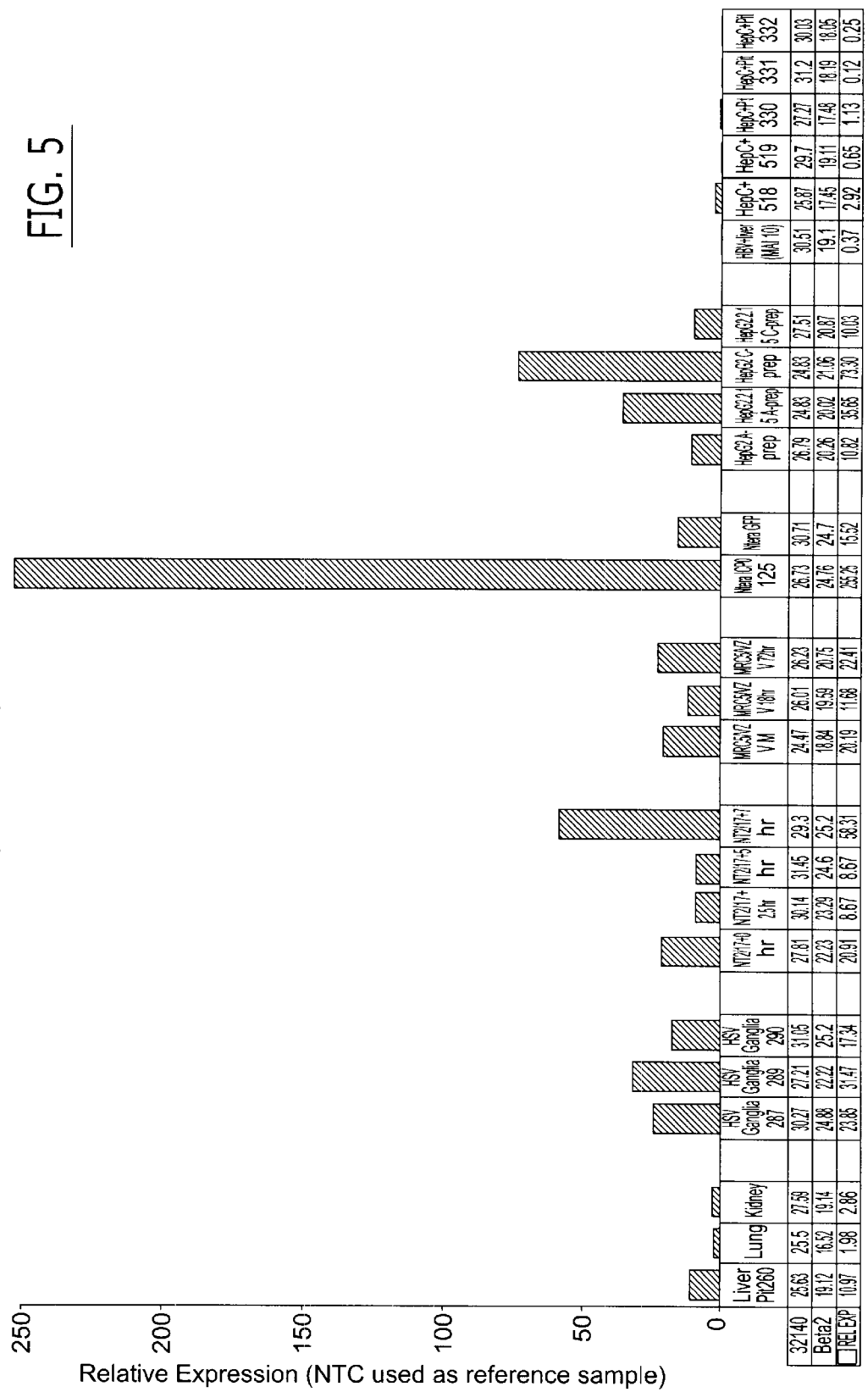
FIG. 5 shows 32140 expression in different tissues. Left to right: First 3 panels are "normal" liver, lung and kidney tissue; next 3 panels show expression in uninfected ganglia (287) and ganglia infected with Herpes Simplex Virus (289 and 290); next 4 panels show a time course of HSV (strain 17+) infection of human Ntera2 neuroblastoma cells (times are 0, 2.5, 5, and 7 hours post-infection); next 3 panels show a time course of Varicella Zoster virus (VZV) infected human MRC5 (lung fibroblast cells) (times are 0, 18 and 72 hours post-infection); next 2 panels are Ntera2 cells infected with an adenovirus that expresses the HSV ICPO transcription factor; next 4 panels show hepatitis B virus (HBV) expressing HepG2.2.15 cells compared to the parental HepG2 cell control; the next 6 panels show HBV-infected and (next 5) hepatitis C virus (HCV)-infected liver samples.
Figure 6:
FIG. 6 shows 32140 expression in Human Panel Phase I showing 32140 expression in various tissues measured by the RNA in each tissue. Gene 32140 is highly expressed in salivary glands and testes, more moderately expressed in brain, small intestine, stomach, spinal cord, and dorsal root ganglia, and it is expressed at lower levels in the other tissues indicated.

The 32140 gene appears to have an important role in viral pathogenesis. In particular, Herpes Simples Virus (HSV) induces expression of the novel 10-formyltetrahydrofolate DH encoded by the gene 32140, particularly in infected neurons. Viral panels have shown that 32140 is induced in HSV-infected mouse ganglia both during active and latent phases. It is induced up to 5-fold in HSV-infected neuroblastoma (Ntera2). 32140 appears to be a 10-formyltetrahydrofolate DH isozyme which is expressed in different tissues (e.g. neuronal tissues) compared to the known 10-formyltetrahydrofolate DH. The 32140 aldehyde dehydrogenase is therfore an important host gene for HSV infection and finds use in the treatment of disorders resulting from Herpes Simples Virus (HSV) and hepatitis B infection. Also, gene 32140 is induced during infection by HSV, but not infection with other viruses such as VZV, HBV,and HCV (FIGS. 4 and 5).

Additional disorders in which the aldehyde dehydrogenase expression is relevant include, but are not limited to the following:

Respiratory viral pathogens and their associated disorders include, for example, adenovirus, resulting in upper and lower respiratory tract infections; conjuctivitis and diarrhea; echovirus, resulting in upper respiratory tract infections, pharyngitis and rash; rhinovirus, resulting in upper respiratory tract infections; cosackievirus, resulting in Pleurodynia, herpangia, hand-foot-mouth disease; coronavirus, resulting in upper respiratory tract infections; influenza A and B viruses, resulting in influenza; parainfluenza virus 1–4, resulting in upper and lower respiratory tract infections and croup; respiratory syncytial virus, resulting in bronchiolitis and pneumonia.

Digestive viral pathogens and their associated disorders include, for example, mumps virus, resulting in mumps, pancreatitis, and orchitis; rotavirus, resulting in childhood diarrhea; Norwalk Agent, resulting in gastroenteritis; hepatitis A virus, resulting in acute viral hepatitis; hepatitis B virus, hepatitis D virus and hepatitis C virus, resulting in acute or chronic hepatitis; hepatitis E virus, resulting in enterically transmitted hepatitis.

Systemic viral pathogens associated with disorders involving skin eruptions include, for example, measles virus, resulting in measles (rubeola); rubella virus, resulting in German measles (rubella); parvovirus, resulting in erythema infectiosum and aplastic anemia; varicella-zoster virus, resulting in chicken pox and shingles; herpes simplex virus 1-associated, resulting in cold sores; and herpes simplex virus 2, resulting in genital herpes.

Systemic viral pathogens associated with hematopoietic disorders include, for example, cytomegalovirus, resulting in cytomegalic inclusion disease; Epstein-Barr virus, resulting in mononucleosis; HTLV-1, resulting in adult T-cell leukemia and tropical spastic paraparesis; HTLV-II; and HIV 1 and HIV 2, resulting in AIDS.

Arboviral pathogens associated with hemorrhagic fevers include, for example, dengue virus 1–4, resulting in dengue and hemorrhagic fever; yellow fever virus, resulting in yellow fever; Colorado tick fever virus, resulting in Colorado tick fever; and regional hemorrhagic fever viruses, resulting in Bolivian, Argentinian, Lassa fever.

Viral pathogens associated with warty growths and other hyperplasias include, for example, papillomavirus, resulting in condyloma and cervical carcinoma; and molluscum virus, resulting in molluscum contagiosum.

Viral pathogens associated with central nervous system disorders include, for example, poliovirus, resulting in poliomyelitis; rabiesvirus, associated with rabies; JC virus, associated with progressive multifocal leukoencephalopathy; and arboviral encephalitis viruses, resulting in Eastern, Western, Venezuelan, St. Louis, or California group encephalitis.

Viral pathogens associated with cancer include, for example, human papillomaviruses, implicated in the genesis of several cancers including squamous cell carcinoma of the cervix and anogenital region, oral cancer and laryngeal cancers; Epstein-Barr virus, implicated in pathogenesis of the African form of Burkitt lymphoma, B-cell lymphomas, Hodgkin disease, and nasopharyngeal carcinomas; hepatitis B virus, implicated in liver cancer; human T-cell leukemia virus type 1 (HTLV-1), associated with T-cell leukemia/lymphoma; and the Kaposi sarcoma herpesvirus (KSHV).

Disorders involving the lung include, but are not limited to, congenital anomalies; atelectasis; diseases of vascular origin, such as pulmonary congestion and edema, including hemodynamic pulmonary edema and edema caused by microvascular injury, adult respiratory distress syndrome (diffuse alveolar damage), pulmonary embolism, hemorrhage, and infarction, and pulmonary hypertension and vascular sclerosis; chronic obstructive pulmonary disease, such as emphysema, chronic bronchitis, bronchial asthma, and bronchiectasis; diffuse interstitial (infiltrative, restrictive) diseases, such as pneumoconioses, sarcoidosis, idiopathic pulmonary fibrosis, desquamative interstitial pneumonitis, hypersensitivity pneumonitis, pulmonary eosinophilia (pulmonary infiltration with eosinophilia), Bronchiolitis obliterans-organizing pneumonia, diffuse pulmonary hemorrhage syndromes, including Goodpasture syndrome, idiopathic pulmonary hemosiderosis and other hemorrhagic syndromes, pulmonary involvement in collagen vascular disorders, and pulmonary alveolar proteinosis; complications of therapies, such as drug-induced lung disease, radiation-induced lung disease, and lung transplantation; tumors, such as bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $a_I$-antitrypsin deficiency, and neonatal hepatitis; intrahepatic biliary tract disease, such as secondary biliary cirrhosis, primary biliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination;

degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytpma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NFI) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused.by calcification, such as calcific aortic stenosis, calcification of a congenitally bicuspid aortic valve, and mitral annular calcification, and myxomatous degeneration of the mitral valve (mitral valve prol apse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving the kidney include, but are not limited to, congenital anomalies including, but not limited to, cystic diseases of the kidney, that include but are not limited to, cystic renal dysplasia, autosomal dominant (adult) polycystic kidney disease, autosomal recessive (childhood) polycystic kidney disease, and cystic diseases of renal medulla, which include, but are not limited to, medullary sponge kidney, and nephronophthisis-uremic medullary cystic disease complex, acquired (dialysis-associated) cystic disease, such as simple cysts; glomerular diseases including pathologies of glomerular injury that include, but are not limited to, in situ immune complex deposition, that includes, but is not limited to, anti-GBM nephritis, Heymann nephritis, and antibodies against planted antigens, circulating immune complex nephritis, antibodies to glomerular cells, cell-mediated immunity in glomerulonephritis, activation of alternative complement pathway, epithelial cell injury, and pathologies involving mediators of glomerular injury including cellular and soluble mediators, acute glomerulonephritis, such as acute proliferative (poststreptococcal, postinfectious) glomerulonephritis, including but not limited to, poststreptococcal glomerulonephritis and nonstreptococcal acute glomerulonephritis, rapidly progressive (crescentic) glomerulonephritis, nephrotic syndrome, membranous glomerulonephritis (membranous nephropathy), minimal change disease (lipoid nephrosis), focal segmental glomerulosclerosis, membranoproliferative glomerulonephritis, IgA nephropathy (Berger disease), focal proliferative and necrotizing glomerulonephritis (focal glomerulonephritis), hereditary nephritis, including but not limited to, Alport syndrome and thin membrane disease (benign familial hematuria), chronic glomerulonephritis, glomerular lesions associated with systemic disease, including but not limited to, systemic lupus erythematosus, Henoch-Schönlein purpura, bacterial endocarditis, diabetic glomerulosclerosis, amyloidosis, fibrillary and immunotactoid glomerulonephritis, and other systemic disorders; diseases affecting tubules and interstitium, including acute tubular necrosis and tubulointerstitial nephritis, including but not limited to, pyelonephritis and urinary tract infection, acute pyelonephritis, chronic pyelonephritis and reflux nephropathy, and tubulointerstitial nephritis induced by drugs and toxins, including but not limited to, acute drug-induced interstitial nephritis, analgesic abuse nephropathy, nephropathy associated with nonsteroidal anti-inflammatory drugs, and other tubulointerstitial diseases including, but not limited to, urate nephropathy, hypercalcemia and nephrocalcinosis, and multiple myeloma; diseases of blood vessels including benign nephrosclerosis, malignant hypertension and accelerated nephrosclerosis, renal artery stenosis, and thrombotic microangiopathies including, but not limited to, classic (childhood) hemolytic-uremic syndrome, adult hemolytic-uremic syndrome/thrombotic thrombocytopenic purpura, idiopathic HUS/TTP, and other vascular disorders including, but not limited to, atherosclerotic ischemic renal disease, atheroembolic renal disease, sickle cell disease nephropathy, diffuse cortical necrosis, and renal infarcts; urinary tract obstruction (obstructive uropathy); urolithiasis (renal calculi, stones); and tumors of the kidney including, but not limited to, benign tumors, such as renal papillary adenoma, renal fibroma or hamartoma (renomedullary interstitial cell tumor), angiomyolipoma, and oncocytoma, and malignant tumors, including renal cell carcinoma (hypernephroma, adenocarcinoma of kidney), which includes urothelial carcinomas of renal pelvis.

Disorders of the breast include, but are not limited to, disorders of development; inflammations, including but not limited to, acute mastitis, periductal mastitis, periductal mastitis (recurrent subareolar abscess, squamous metaplasia of lactiferous ducts), mammary duct ectasia, fat necrosis, granulomatous mastitis, and pathologies associated with silicone breast implants; fibrocystic changes; proliferative breast disease including, but not limited to, epithelial hyperplasia, sclerosing adenosis, and small duct papillomas; tumors including, but not limited to, stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, no special type, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Disorders involving the testis and epididymis include, but are not limited to, congenital anomalies such as cryptorchidism, regressive changes such as atrophy, inflammations such as nonspecific epididymitis and orchitis, granulomatous (autoimmune) orchitis, and specific inflammations including, but not limited to, gonorrhea, mumps, tuberculosis, and syphilis, vascular disturbances including torsion, testicular tumors including germ cell tumors that include, but are not limited to, seminoma, spermatocytic seminoma, embryonal carcinoma, yolk sac tumor choriocarcinoma, teratoma, and mixed tumors, tumors of sex cord-gonadal stroma including, but not limited to, Leydig (interstitial) cell tumors and sertoli cell tumors (androblastoma), and testicular lymphoma, and miscellaneous lesions of tunica vaginalis.

The 32140 protein, fragments thereof, and derivatives and other variants of the sequence in SEQ ID NO:2 are collectively referred to as "polypeptides or proteins of the invention" or "32140 polypeptides or proteins". Nucleic acid molecules encoding such polypeptides or proteins are collectively referred to as "nucleic acids of the invention" or "32140 nucleic acids." 32140 molecules refer to 32140 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6× sodium chloride/sodium citrate (SSC) at about 45° C., followed by one or more washes in 0.2×SSC, 0.1% SDS at 50° C. Another example of stringent hybridization conditions are hybridization in 6× sodium chloride/sodium citrate (SSC) at about 45° C., followed by one or more washes in 0.2× SSC, 0.1% SDS at 55° C. A further example of stringent hybridization conditions is hybridization in 6× sodium chloride/sodium citrate (SSC) at about 45° C., followed by one or more washes in 0.2×SSC, 0.1% SDS at 60° C. Preferably, stringent hybridization conditions are hybridization in 6× sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 32140 protein, preferably a mammalian 32140 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 32140 protein having less than about 30%, 20%, 10% and more preferably 5% (by dry weight), of non-32140 protein (also referred to herein as a "contaminating protein"), or of chemical precursors or non-32140 chemicals. When the 32140 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 32140(e.g., the sequence of SEQ ID NO:1, SEQ ID NO:3, or the nucleotide sequence of the DNA insert of the plasmid deposited with ATCC as Accession Number PTA-3424) without abolishing or more preferably, without substantially altering a biological activity, whereas an "essential" amino acid residue results in such a change. For example, amino acid residues that are conserved among the polypeptides of the present invention, e.g., those present in the aldehyde dehydrogenase domain, are predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 32140 protein is preferably replaced with another amino acid residue from the same side chain family. Alternatively, in another embodiment, mutations can be introduced randomly along all or part of a 32140 coding sequence, such as by saturation mutagenesis, and the resultant mutants can be screened for 32140 biological activity to identify mutants that retain activity. Following mutagenesis of SEQ ID NO:1, SEQ ID NO:3, or the nucleotide sequence of the DNA insert of the plasmid deposited with ATCC as Accession Number PTA-3424, the encoded protein can be expressed recombinantly and the activity of the protein can be determined.

As used herein, a "biologically active portion" of a 32140 protein includes a fragment of a 32140 protein which participates in an interaction between a 32140 molecule and a non-32140 molecule. Biologically active portions of a 32140 protein include peptides comprising amino acid sequences sufficiently homologous to or derived from the amino acid sequence of the 32140 protein, e.g., the amino acid sequence shown in SEQ ID NO:2, which include less amino acids than the full length 32140 proteins, and exhibit at least one activity of a 32140 protein. Typically, biologically active portions comprise a domain or motif with at least one activity of the 32140 protein, e.g., aldehyde dehydrogenase activity. A biologically active portion of a 32140 protein can be a polypeptide which is, for example, 10, 25, 50, 100, 200 300, 400, 500, 600, 700, 800, or more amino acids in length. Biologically active portions of a 32140 protein can be used as targets for developing agents which modulate a 32140 mediated activity, e.g., aldehyde dehydrogenase activity.

Calculations of homology or sequence. identity between sequences (the terms are used interchangeably herein) are performed as follows.

To determine the percent identity of two amino acid sequences, or of two nucleic acid sequences, the sequences.are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 32140 amino acid sequence of SEQ ID NO:2 having 277 amino acid residues, at least 369, preferably at least 462, more preferably at least 554, even more preferably at least 646, and even more preferably at least 738, 831 or 923 amino acid residues are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http:/www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (CABIOS, 4:11–17 (1989)) which has been incorporated into the ALIGN program (version 2.0), using a PAM120 weight residue table, a gap length penalty of 12 and a gap. penalty of 4.

The nucleic acid and protein sequences described herein can be used as a "query sequence" to perform a search against public databases to, for example, identify other family members or related sequences. Such searches can be performed using the NBLAST and XBLAST programs (version. 2.0) of Altschul, et al., (1990) *J. Mol. Biol.* 215:403–10. BLAST nucleotide searches can be performed with the NBLAST program, score=100, wordlength=12 to obtain nucleotide sequences homologous to 32140 nucleic acid molecules of the invention. BLAST protein searches can be performed with the XBLAST program, score=50, wordlength=3 to obtain amino acid sequences homologous to 32140 protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 32140 polypeptide described herein, e.g., a full length 32140 protein or a fragment thereof, e.g., a biologically active portion of 32140 protein. Also included is a nucleic acid fragment suitable for use as a hybridization probe, which can be used, e.g., to a identify nucleic acid molecule encoding a polypeptide of the invention, 32140 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or the nucleotide sequence of the DNA insert of the plasmid deposited with ATCC as Accession Number PTA-3424, or a portion of any of these nucleotide sequences. In one embodiment, the nucleic acid molecule includes sequences encoding the human 32140 protein (i.e., "the coding region", from nucleotides 129–2897 of SEQ ID NO:1, not including the terminal codon), as well as 5' untranslated sequences (nucleotides 1–128 of SEQ ID NO:1). Alternatively, the nucleic acid molecule can include only the coding region of SEQ ID NO:1 (e.g., nucleotides 129–2897 of SEQ ID NO:1, corresponding to SEQ ID NO:3) and, e.g., no flanking sequences which normally accompany the subject sequence. In another embodiment, the nucleic acid molecule encodes a sequence corresponding to the mature protein of SEQ ID NO:2.

In another embodiment, an isolated nucleic acid molecule of the invention includes a nucleic acid molecule which is a complement of the nucleotide sequence shown in SEQ ID NO:1, SEQ ID NO:3, or the nucleotide sequence of the DNA insert of the plasmid deposited with ATCC as Accession Number PTA-3424, or a portion of any of these nucleotide sequences. In other embodiments, the nucleic acid molecule of the invention is sufficiently complementary to the nucleotide sequence shown in SEQ ID NO:1, SEQ ID NO:3, or the nucleotide sequence of the DNA insert of the plasmid deposited with ATCC as Accession Number PTA-3424 such that it can hybridize to the nucleotide sequence shown in SEQ ID NO:1, SEQ ID NO:3, or the nucleotide sequence of the DNA insert of the plasmid deposited with ATCC as Accession Number PTA-3424, thereby forming a stable duplex.

In one embodiment, an isolated nucleic acid molecule of the present invention includes a nucleotide sequence which is at least about 60%, 65%, 70%, 75%, 80%, 85%, 90%, 91%, 92%, 93%, 94%, 95%, 96%, 97%, 98%, 99%, or more homologous to the nucleotide sequence shown in SEQ ID NO:1, SEQ ID NO:3, or the nucleotide sequence of the DNA insert of the plasmid deposited with ATCC as Accession Number PTA-3424. In the case of an isolated nucleic acid molecule which is longer than or equivalent in length to the reference sequence, e.g., SEQ ID NO:1, or SEQ ID NO:3, the comparison is made with the full length of the reference sequence. Where the isolated nucleic acid molecule is shorter than the reference sequence, e.g., shorter than SEQ ID NO:1, or SEQ ID NO:3, the comparison is made to a segment of the reference sequence of the same length (excluding any loop required by the homology calculation).

32140 Nucleic Acid Fragments

A nucleic acid molecule of the invention can include only a portion of the nucleic acid sequence of SEQ ID NO:1, SEQ ID NO:3, or the nucleotide sequence of the DNA insert of the plasmid deposited with ATCC as Accession Number PTA-3424. For example, such a nucleic acid molecule can include a fragment which can be used as a probe or primer or a fragment encoding a portion of a 32140 protein, e.g., an immunogenic or biologically active portion of a 32140 protein. A fragment can comprise: nucleotides 129–2897 of SEQ ID NO:1, which encodes an aldehyde dehydrogenase domain of human 32140. The nucleotide sequence determined from the cloning of the 32140 gene allows for the generation of probes and primers designed for use in identifying and/or cloning other 32140 family members, or fragments thereof, as well as 32140 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an aldehyde dehydrogenase domain. In a preferred embodiment the fragment is at least, 50, 100, 200, 300, 400, 500, 600, 700, or 900 base pairs in length.

32140 probes and primers are provided. Typically a probe/primer is an isolated or purified oligonucleotide. The oligonucleotide typically includes a region of nucleotide sequence that hybridizes under stringent conditions to at least about 7, 12 or 15, preferably about 20 or 25, more preferably about 30, 35, 40, 45, 50, 55, 60, 65, or 75 consecutive nucleotides of a sense or antisense sequence of SEQ ID NO:1, SEQ ID NO:3, or the nucleotide sequence of the DNA insert of the plasmid deposited with ATCC as Accession Number PTA-3424, or of a naturally occurring allelic variant or mutant of SEQ ID NO:1, SEQ ID NO:3, or the nucleotide sequence of the DNA insert of the plasmid deposited with ATCC as Accession Number PTA-3424.

In a preferred embodiment the nucleic acid is a probe which is at least 5 or 10, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes an aldehyde dehydrogenase domain (e.g., about amino acid residues 450–923 of SEQ ID NO:2).

In another embodiment a set of primers is provided, e.g., primers suitable for use in a PCR, which can be used to amplify a selected region of a 32140 sequence, e.g., a region described herein. The primers should be at least 5, 10, or 50 base pairs in length and less than 100, or less than 200, base pairs in length. The primers should be identical, or differ by one base from a sequence disclosed herein or from a naturally occurring variant. E.g., primers suitable for amplifying all or a portion of any of the following regions are provided: an aldehyde dehydrogenase domain (e.g., about amino acid residues 450–923 of SEQ ID NO:2).

A nucleic acid fragment can encode an epitope bearing region of a polypeptide described herein.

A nucleic acid fragment encoding a "biologically active portion of a 32140 polypeptide" can be prepared by isolating a portion of the nucleotide sequence of SEQ ID NO:1, SEQ ID NO:3, or the nucleotide sequence of the DNA insert of the plasmid deposited with ATCC as Accession Number PTA-3424, which encodes a polypeptide having a 32140 biological activity (e.g., the biological activities of the 32140 proteins as described herein), expressing the encoded portion of the 32140 protein (e.g., by recombinant expression in vitro) and assessing the activity of the encoded portion of the 32140 protein. For example, a nucleic acid fragment encoding a biologically active portion of 32140 includes an aldehyde dehydrogenase domain (e.g., about amino acid residues 450–923 of SEQ ID NO:2). A nucleic acid fragment encoding a biologically active portion of a 32140 polypeptide, may comprise a nucleotide sequence which is greater than 300–1200 or more nucleotides in length.

In preferred embodiments, nucleic acids include a nucleotide sequence which is about 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, or 7200 nucleotides in length and hybridizes under stringent hybridization conditions to a nucleic acid molecule of SEQ ID NO:1, or SEQ ID NO:3, or the nucleotide sequence of the DNA insert of the plasmid deposited with ATCC as Accession Number PTA-3424.

32140 Nucleic Acid Variants

The invention further encompasses nucleic acid molecules th differ from the nucleotid &-sequence shown in SEQ ID NO:1, SEQ ID NO:3, or the nucleotide sequence of the DNA insert of the plasmid deposited with ATCC as Accession Number PTA-3424. Such differences can be due to degeneracy of the genetic code (and result in a nucleic acid which encodes the same 32140 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that shown in SEQ ID NO:2. If alignment is needed for this comparison the sequences should be aligned for maximum homology. "Looped" out sequences from deletions or insertions, or mismatches, are considered differences.

Nucleic acids of the invention can be chosen for having codons, which are perferred, or non preferred, for a particular expression system. E.g., the nucleic acid can be one in which at least one colon, at preferably at least 10%, or 20% of the codons has been alterd such that the sequence is optimized for expression in E. co;i, yeast, human, insect, or CHO cell.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1, SEQ ID NO:3, or the nucleotide sequence of the DNA insert of the plasmid deposited with ATCC as Accession Number PTA-3424, e.g., as follows: by at least one but less than 10, 20, 30, or 40 nucleotides; at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is 50%, at least about 55%, typically at least about 70–75%, more typically at least about 80–85%, and most typically at least about 90–95% or more identical to the amino acid sequence shown in SEQ ID NO:2 or a fragment of this sequence. Such nucleic acid molecules can readily be obtained as being able to hybridize under stringent conditions, to the nucleotide sequence shown in SEQ ID NO:3 or a fragment of this sequence. Nucleic acid molecules corresponding to orthologs, homologs, and allelic variants of the 32140 cDNAs of the invention can further be isolated by mapping to the same chromosome or locus as the 32140 gene. Preferred variants include those that are correlated with aldehyde dehydrogenase activity.

Allelic variants of 32140, e.g., human 32140, include both functional and non-functional proteins. Functional allelic variants are naturally occurring amino acid sequence variants of the 32140 protein within a population that maintain the ability to modulate the oxidation of aldehydes. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 32140, e.g., human 32140, protein within a population that do not have the ability to oxidize aldehydes. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 32140 family members and, thus, which have anucleotide sequence which differs from the 32140 sequences ofSEQ ID NO:1, SEQ ID NO:3, or the nucleotide sequence of the DNA insert of the plasmid deposited with ATCC as Accession Number PTA-3424 are intended to be within the scope of the invention.

Antisense Nucleic Acid Molecules, Ribozymes and Modified 32140 Nucleic Acid Molecules In another aspect, the invention features, an isolated nucleic acid molecule which is antisense to 32140. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 32140 coding strand, or to only a portion thereof (e.g., the coding region of human 32140 corresponding to SEQ ID NO:3). In another embodiment, the antisense nucleic acid molecule is antisense to a "noncoding region" of the coding strand of a nucleotide sequence encoding 32140 (e.g., the 5' and 3' untranslated regions).

An antisense nucleic acid can be designed such that it is complementary to the entire coding region of 32140 mRNA, but more preferably is an oligonucleotide which is antisense to only a portion of the coding or noncoding region of 32140 mRNA. For example, the antisense oligonucleotide can be complementary to the region surrounding the translation start site of 32140 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 32140 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., (1987) *Nucleic Acids. Res.* 15:6625–6641). The antisense nucleic acid molecule can also comprise a 2'-o-methylribonucleotide (Inoue et al., (1987) *Nucleic Acids Res.* 15:6131–6148) or a chimeric RNA-DNA analogue (Inoue et al., (1987) *FEBS Lett.* 215:327–330).

In still another embodiment, an antisense nucleic acid of the invention is a ribozyme. A ribozyme having specificity for a 32140-encoding nucleic acid can include one or more sequences complementary to the nucleotide sequence of a 32140 cDNA disclosed herein (i.e., SEQ ID NO:1, or SEQ ID NO:3), and a sequence having known catalytic sequence responsible for mRNA cleavage (see U.S. Pat. No. 5,093, 246 or Haselhoff and Gerlach, (1988) *Nature* 334:585–591). For example, a derivative of a Tetrahymena L-19 IVS RNA can be constructed in which the nucleotide sequence of the active site is complementary to the nucleotide sequence to be cleaved in a 32140-encoding mRNA. See, e.g., Cech et al. U.S. Pat. No. 4,987,071; and Cech et al. U.S. Pat. No. 5,116,742. Alternatively, 32140 mRNA can be used to select a catalytic RNA having a specific ribonuclease activity from a pool of RNA molecules. See, e.g., Bartel, D. and Szostak, J. W. (1993) *Science* 261:1411–1418.

32140 gene expression can be inhibited by targeting nucleotide sequences complementary to the regulatory region of the 32140 (e.g., the 32140 promoter and/or enhancers) to form triple helical structures that prevent transcription of the 32140 gene in target cells. See generally, Helene, C., (1991) *Anticancer Drug Des.* 6:569–84; Helene, C. et al., (1992) *Ann. N.Y. Acad. Sci.* 660:27–36; and Maher, L. J., (1992) Bioassays 14:807–15. The potential sequences that can be targeted for triple helix formation can be increased by creating a so-called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 32140 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al., (1996) *Bioorganic & Medicinal Chemistry* 4: 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup B. et al., (1996) supra; Perry-O'Keefe et al., *Proc. Natl. Acad. Sci.* 93: 14670–675.

PNAs of 32140 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 32140 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., (1996) supra)); or as probes or primers for DNA sequencing or hybridization (Hyrup B. et al., (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al., (1989) *Proc. Natl. Acad. Sci. USA* 86:6553–6556; Lemaitre et al., (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al., (1988) *Bio-Techniques* 6:958–976) or intercalating agents. (See, e.g., Zon, (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 32140 nucleic acid of the invention, two complementary regions one having a fluorophore and one a quencher such that the molecular beacon is useful for quantitating the presence of the 32140 nucleic acid of the invention in a sample. Molecular beacon nucleic acids are described, for example, in Lizardi et al., U.S. Pat. No. 5,854,033; Nazarenko et al., U.S. Pat. No. 5,866,336, and Livak et al., U.S. Pat. No. 5,876,930.

Isolated 32140 Polypeptides

In another aspect, the invention features, an isolated 32140 protein, or fragment, e.g., a biologically active portion, for use as immunogens or antigens to raise or test (or more generally to bind) anti-32140 antibodies. 32140 protein can be isolated from cells or tissue sources using standard protein purification techniques. 32140 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 32140 polypeptide has one or more of the following characteristics:

(i) it catalyzes the oxidation of aldehydes;

(ii) it has a molecular weight, e.g., a deduced molecular weight, amino acid composition or other physical characteristic of the polypeptide of SEQ ID NO:2;

(iii) it has an overall sequence similarity of at least 50%, preferably at least 60%, more preferably at least 70, 80, 90, or 95%, with a polypeptide of SEQ ID NO:2;

(iv) it has an aldehyde dehydrogenase domain which preferably has an overall sequence similarity of about 70%, 80%, 90% or 95% with amino acid residues 450–923 of SEQ ID NO:2;

(v) it has at least 70%, preferably 80%, and most preferably 95% of the cysteines found amino acid sequence of the native protein.

In a preferred embodiment the 32140 protein, or fragment thereof, differs from the corresponding sequence in SEQ ID NO:2. In one embodiment it differs by at least one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the aldehyde dehydrogenase domain. In another preferred embodiment one or more differences are in non-active site residues, e.g. outside of the aldehyde dehydrogenase domain.

Other embodiments include a protein that contain one or more changes in amino acid sequence, e.g., a change in an amino acid residue which is not essential for activity. Such 32140 proteins differ in amino acid sequence from SEQ ID NO:2, yet retain biological activity.

In one embodiment, a biologically active portion of a 32140 protein includes an aldehyde dehydrogenase domain. In another embodiment, a biologically active portion of a 32140 protein includes a formyl transferase domain. Moreover, other biologically active portions, in which other regions of the protein are deleted, can be prepared by recombinant techniques and evaluated for one or more of the functional activities of a native 32140 protein.

In a preferred embodiment, the 32140 protein has an amino acid sequence shown in SEQ ID NO:2. In other embodiments, the 32140 protein is substantially identical to SEQ ID NO:2. In yet another embodiment, the 32140 protein is substantially identical to SEQ ID NO:2 and retains the functional activity of the protein of SEQ ID NO:2, as described in detail above. Accordingly, in another embodiment, the 32140 protein is a protein which includes an amino acid sequence at least about 60%, 65%, 70%, 75%, 80%, 85%, 90%, 95%, 98% or more identical to SEQ ID NO:2.

32140 Chimeric or Fusion Proteins

In another aspect, the invention provides 32140 chimeric or fusion proteins. As used herein, a 32140 "chimeric protein" or "fusion protein" includes a 32140 polypeptide linked to a non-32140 polypeptide. A "non-32140 polypeptide" refers to a polypeptide having an amino acid sequence corresponding to a protein which is not substantially homologous to the 32140 protein, e.g., a protein which is different from the 32140 protein and which is derived from the same or a different organism. The 32140 polypeptide of the fusion protein can correspond to all or a portion e.g., a fragment described herein of a 32140 amino acid sequence. In a preferred embodiment, a 32140 fusion protein includes at least one (or two) biologically active portion of a 32140 protein. The non-32140 polypeptide can be fused to the N-terminus or C-terminus of the 32140 polypeptide.

The fusion protein can include a moiety which has a high affinity for a ligand. For example, the fusion protein can be a GST-32140 fusion protein in which the 32140 sequences are fused to the C-terminus of the GST sequences. Such fusion proteins can facilitate the purification of recombinant 32140. Alternatively, the fusion protein can be a 32140 protein containing a heterologous signal sequence at its N-terminus. In certain host cells (e.g., mammalian host cells), expression and/or secretion of 32140 can be increased through use of a heterologous signal sequence.

Fusion proteins can include all or a part of a serum protein, e.g., an IgG constant region, or human serum albumin.

The 32140 fusion proteins of the invention can be incorporated into pharmaceutical compositions and administered to a subject in vivo. The 32140 fusion proteins can be used to affect the bioavailability of a 32140 substrate. 32140 fusion proteins may be useful therapeutically for the treatment of disorders caused by, for example, (i) aberrant modification or mutation of a gene encoding a 32140 protein; (ii) misregulation of the 32140 gene; and (iii) aberrant post-translational modification of a 32140 protein.

Moreover, the 32140-fusion proteins of the invention can be used as immunogens to produce anti-32140 antibodies in a subject, to purify 32140 ligands and in screening assays to identify molecules which inhibit the interaction of 32140 with a 32140 substrate.

Expression vectors are commercially available that already encode a fusion moiety (e.g., a GST polypeptide). A 32140-encoding nucleic acid can be cloned into such an expression vector such that the fusion moiety is linked in-frame to the 32140 protein.

Variants of 32140 Proteins

In another aspect, the invention also features a variant of a 32140 polypeptide, e.g., which functions as an agonist (mimetics) or as an antagonist. Variants of the 32140 proteins can be generated by mutagenesis, e.g., discrete point mutation, the insertion or deletion of sequences or the truncation of a 32140 protein. An agonist of the 32140 proteins can retain substantially the same, or a subset, of the biological activities of the naturally occurring form of a 32140 protein. An antagonist of a 32140 protein can inhibit one or more of the activities of the naturally occurring form of the 32140 protein by, for example, competitively modulating a 32140-mediated activity of a 32140 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 32140 protein.

Variants of a 32140 protein can be identified by screening combinatorial libraries of mutants, e.g., truncation mutants, of a 32140 protein for agonist or antagonist activity.

Libraries of fragments e.g., N terminal, C. terminal, or internal fragments, of a 32140 protein coding sequence can be used to generate a variegated population of fragments for screening and subsequent selection of variants of a 32140 protein.

Variants in which a cysteine residues is added or deleted or in which a residue which is glycosylated is added or deleted are particularly preferred.

Methods for screening gerie products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 32140. variants (Arkin and Yourvan, (1992) *Proc. Natl. Acad. Sci. USA* 89:7811–7815; Delgrave et al., (1993) *Protein Engineering* 6:327–331).

Cell based assays can be exploited to analyze a variegated 32140 library. For example, a library of expression vectors can be transfected into a cell line, e.g., a cell line, which ordinarily responds to 32140 in a substrate-dependent manner. The transfected cells are then contacted with 32140 and the effect of the expression of the mutant on signaling by the 32140 substrate can be detected, e.g., by measuring aldehyde dehydrogenase activity. Plasmid DNA can then be recovered from the cells which score for inhibition, or alternatively, potentiation of signaling by the 32140 substrate, and the individual clones further characterized.

In another aspect, the invention features a method of making a 32140 polypeptide, e.g., a peptide having a non-wild type activity, e.g., an antagonist, agonist, or super agonist of a naturally occurring 32140 polypeptide, e.g., a naturally occurring 32140 polypeptide. The method includes: altering the sequence of a 32140 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 32140 polypeptide a biological activity of a naturally occurring 32140 polypeptide. The method includes: altering the sequence, e.g., by substitution or deletion of one or more residues, of a 32140 polypeptide, e.g., altering the sequence of a non-conserved region, or a domain or residue described herein, and testing the altered polypeptide for the desired activity.

Anti-32140 Antibodies

In another aspect, the invention provides an anti-32140 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 32140 protein or, antigenic peptide fragment of 32140 can be used as an immunogen or can be used to identify anti-32140 antibodies made with other immunogens, e.g., cells, membrane preparations, and the like. The antigenic peptide of 32140 should include at least 8 amino acid residues of the amino acid sequence shown in SEQ ID NO:2 and encompasses an epitope of 32140. Preferably, the antigenic peptide includes at least 10 amino acid residues, more preferably at least 15 amino acid residues, even more preferably at least 20 amino acid residues, and most preferably at least 30 amino acid residues.

Fragments of 32140 which include, e.g., residues 200–235 of SEQ ID NO:2 of SEQ ID NO:5 can be used to make, e.g., used as immunogens, or used to characterize the specificity of an antibody or antibodies against what are believed to be hydrophilic regions of the 32140 protein. Similarly, a fragment of 32140 which includes, e.g., residues 585–635 of SEQ ID NO:2 can be used to make an antibody against what is believed to be a hydrophobic region of the 32140 protein; a fragment of 32140 which includes residues 450–923, or 669–728 of SEQ ID NO:2 can be used to make an antibody against the aldehyde dehydrogenase region of the 32140 protein.

Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of 32140 are located on the surface of the protein, e.g., hydrophilic regions, as well as regions with high antigenicity. For example, an Emini surface probability analysis of the human 32140 protein sequence can be used to indicate the regions that have a particularly high probability of being localized to the surface of the 32140 protein and are thus likely to constitute surface residues useful for targeting antibody production.

In a preferred embodiment the antibody binds an epitope on any domain or region on 32140 proteins described herein.

Chimeric, humanized, but most preferably, completely human antibodies are desirable for applications which include repeated administration, e.g., therapeutic treatment (and some diagnostic applications) of human patients.

The anti-32140 antibody can be a single chain antibody. A single-chain antibody (scFV) may be engineered (see, for example, Colcher, D. et al., *Ann. NY Acad. Sci.* 1999 Jun 30;880:263–80; and Reiter, Y., *Clin. Cancer Res.* 1996 Feb;2(2):245–52). The single chain antibody can be dimerized or multimerized to generate multivalent antibodies having specificities for different epitopes of the same target 32140 protein.

An anti-32140 antibody (e.g., monoclonal antibody) can be used to isolate 32140 by standard techniques, such as affinity chromatography or immunoprecipitation. Moreover, an anti-32140 antibody can be used to detect 32140 protein (e.g., in a cellular lysate or cell supernatant) in order to evaluate the abundance and pattern of expression of the protein. Anti-32140 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 32140 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 32140 proteins, mutant forms of 32140 proteins, fusion proteins, and the like).

The recombinant expression vectors of the invention can be designed for expression of 32140 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S., (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 32140 activity assays, (e.g., direct assays or competitive assays described in detail below), or to generate antibodies specific for 32140 proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six (6) weeks).

To maximize recombinant protein expression in *E. coli* is to express the protein in host bacteria with an impaired capacity to proteolytically cleave the recombinant protein (Gottesman, S., *Gene Expression Technology: Methods in Enzymology* 185, Academic Press, San Diego, California (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

The 32140 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al., (1987) *Genes Dev.* 1:268–277), lymphoid-specific promoters (Calame and Eaton, (1988) *Adv. Immunol.* 43:235–275), in particular promoters of T cell receptors (Winoto and Baltimore, (1989) *EMBO J.* 8:729–733) and immunoglobulins (Banerji et al., (1983) *Cell* 33:729–740; Queen and Baltimore, (1983) *Cell* 33:741–748), neuron-specific promoters (e.g., the neurofilament promoter; Byrne and Ruddle, (1989) *Proc. Natl. Acad. Sci. USA* 86:5473–5477), pancreas-specific promoters (Edlund et al., (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, (1990) *Science* 249:374–379) and the α-fetoprotein promoter (Campes and Tilghman, (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect the invention provides a host cell which includes a nucleic acid molecule described herein, e.g., a 32140 nucleic acid molecule within a recombinant expression vector or a 32140 nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 32140 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation A host cell of the invention can be used to produce (i.e., express) a 32140 protein. Accordingly, the invention further provides methods for producing a 32140 protein using the host cells of the invention. In one embodiment, the method includes culturing the host cell of the invention (into which a recombinant expression vector encoding a 32140 protein has been introduced) in a suitable medium such that a 32140 protein is produced. In another embodiment, the method further includes isolating a 32140 protein from the medium or the host cell.

In another aspect, the invention features, a cell or purified preparation of cells which include a 32140 transgene, or which otherwise misexpress 32140. The cell preparation can consist of human or non-human cells, e.g., rodent cells, e.g., mouse or rat cells, rabbit cells, or pig cells. In preferred embodiments, the cell or cells include a 32140 transgene, e.g., a heterologous form of a 32140, e.g., a gene derived from humans (in the case of a non-human cell). The 32140 transgene can be misexpressed, e.g., overexpressed or underexpressed. In other preferred embodiments, the cell or cells include a gene which misexpress an endogenous 32140, e.g., a gene the expression of which is disrupted, e.g., a knockout. Such cells can serve as a model for studying disorders which are related to mutated or misexpressed 32140 alleles or for use in drug screening.

In another aspect, the invention features, a human cell, e.g., a hematopoietic stem cell, transformed with nucleic acid which encodes a subject 32140 polypeptide.

Also provided are cells or a purified preparation thereof, e.g., human cells, in which an endogenous 32140 is under the control of a regulatory sequence that does not normally control the expression of the endogenous 32140 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 32140 gene. For example, an endogenous 32140 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombination can be used to insert the heterologous DNA as described in, e.g., Chappel, U.S. Pat. No. 5,272,071; WO 91/06667, published on May 16, 1991.

Transgenic Animals

The invention provides non-human transgenic animals. Such animals are useful for studying the function and/or activity of a 32140 protein and for identifying and/or evaluating modulators of 32140 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 32140 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 32140 protein to particular cells. A transgenic founder animal can be identified based upon the presence of a 32140 transgene in its genome and/or expression of 32140 mRNA in tissues or cells of the animals. A transgenic founder animal can then be used to breed additional animals carrying the transgene. Moreover, transgenic animals carrying a transgene encoding a 32140 protein can further be bred to other transgenic animals carrying other transgenes.

32140 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). The isolated nucleic acid molecules of the invention can be used, for example, to express a 32140 protein (e.g., via a recombinant expression vector in a host cell in gene therapy applications), to detect a 32140 mRNA (e.g., in a biological sample) or a genetic alteration in a 32140 gene, and to modulate 32140 activity, as described further below. The 32140 proteins can be used to treat disorders characterized by insufficient or excessive production of a 32140 substrate or production of 32140 inhibitors. In addition, the 32140 proteins can be used to screen for naturally occurring 32140 substrates, to screen for drugs or compounds which modulate 32140 activity, as well as to treat disorders characterized by insufficient or excessive production of 32140 protein or production of 32140 protein forms which have decreased, aberrant or unwanted activity compared to 32140 wild-type protein. Such disorders include those characterized by the failure to oxidize aldehydes. Moreover, the anti-32140 antibodies of the invention can be used to detect and isolate 32140 proteins, regulate the bioavailability of 32140 proteins, and modulate 32140 activity.

A method of evaluating a compound for the ability to interact with, e.g., bind, a subject 32140 polypeptide is provided. The method includes: contacting the compound with the subject 32140 polypeptide; and evaluating ability of the compound to interact with, e.g., to bind or form a complex with the subject 32140 polypeptide. This method can be performed in vitro, e.g., in a cell free system, or in vivo, e.g., in a two-hybrid interaction trap assay. This method can be used to identify naturally occurring molecules which interact with subject 32140 polypeptide. It can also be used to find natural or synthetic inhibitors of subject 32140 polypeptide. Screening methods are discussed in more detail below.

Screening Assays:

The invention provides methods (also referred to herein as "screening assays") for identifying modulators, i.e., candidate or test compounds or agents (e.g., proteins, peptides, peptidomimetics, peptoids, small molecules or other drugs) which bind to 32140 proteins, have a stimulatory or inhibitory effect on, for example, 32140 expression or 32140 activity, or have a stimulatory or inhibitory effect on, for example, the expression or activity of a 32140 substrate. Compounds thus identified can be used to modulate the activity of target gene products (e.g., 32140 genes) in a therapeutic protocol, to elaborate the biological function of the target gene product, or to identify compounds that disrupt normal target gene interactions.

In one embodiment, the invention provides assays for screening candidate or test compounds which are substrates of a 32140 protein or polypeptide or a biologically active portion thereof. In another embodiment, the invention provides assays for. screening candidate or test compounds which bind to or modulate the activity of a 32140 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann, R. N. et al., *J. Med. Chem.* 1994, 37: 2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al., (1994) *Proc. Natl. Acad. Sci. USA* 91:11422; Zuckermann et al., (1994). *J. Med. Chem.* 37:2678; Cho et al., (1993) *Science* 261:1303; Carrell et al., (1994) *Angew. Chem. Int. Ed. Engl.* 33:2059; Carell et al., (1994) *Angew. Chem. Int. Ed. Engl.* 33:2061; and in Gallop et al., (1994) *J. Med. Chem.* 37:1233.

Libraries of compounds may be presented in solution (e.g., Houghten, (1992) *Biotechniques* 13:412–421), or on beads (Lam, (1991) *Nature* 354:82–84), chips (Fodor, (1993) *Nature* 364:555–556), bacteria or spores (Ladner, U.S. Pat. No. 5,223,409), plasmids (Cull et al., (1992) *Proc. Natl. Acad. Sci. USA* 89:1865–1869) or on phage (Scott and Smith, (1990) *Science* 249:386–390); (Devlin, (1990) *Science* 249:404–406); (Cwirla et al., (1990) *Proc. Natl. Acad. Sci.* 87:6378–6382); (Felici, (1991) *J. Mol. Biol.* 222:301–310); (Ladner supra.).

In one embodiment, an assay is a cell-based assay in which a cell which expresses a 32140 protein or biologically active portion thereof is contacted with a test compound, and the ability of the test compound to modulate 32140 activity is determined. Determining the ability of the test compound to modulate 32140 activity can be accomplished by monitoring, for example, aldehyde dehydrogenase activity. The cell, for example, can be of mammalian origin, e.g., human. Cell homogenates, or fractions, preferably membrane containing fractions, can also be tested.

The ability of the test compound to modulate 32140 binding to a compound, e.g., a 32140 substrate, or to bind to 32140 can also be evaluated. This can be accomplished, for example, by coupling the compound, e.g., the substrate, with a radioisotope or enzymatic label such that binding of the compound, e.g., the substrate, to 32140 can be determined by detecting the labeled compound, e.g., substrate, in a complex. Alternatively, 32140 could be coupled with a radioisotope or enzymatic label to monitor the ability of a test compound to modulate 32140 binding to a 32140 substrate in a complex. For example, compounds (e.g., 32140 substrates) can be labeled with $^{125}$I, $^{35}$S, $^{14}$C, or $^{3}$H, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 32140 substrate) to interact with 32140 with or without the labeling of any of the interactants can be evaluated. For example, a microphysiometer can be used to detect the interaction of a compound with 32140 without the labeling of either the compound or the 32140. McConnell, H. M. et al., (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 32140.

In yet another embodiment, a cell-free assay is provided in which a 32140 protein or biologically active portion thereof is contacted with a test compound and the ability of the test compound to bind to the 32140 protein or biologically active portion thereof is evaluated. Preferred biologically active portions of the 32140 proteins to be used in assays of the present invention include fragments which participate in interactions with non-32140 molecules, e.g., fragments with high surface probability scores.

Soluble and/or membrane-bound forms of isolated proteins (e.g., 32140 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3 cholamidopropyl)dimethylamminio]-1-propane sulfonate (CHAPS), 3-[(3-cholamidopropyl) dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block aldehyde dehydrogenase activity within a cell is evaluated.

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 32140 protein to bind to a target molecule can be accomplished using real-time Biomolecular Interaction Analysis (BIA) (see, e.g., Sjolander, S. and Urbaniczky, C., (1991) *Anal. Chem.* 63:2338–2345 and Szabo et al., (1995) *Curr. Opin. Struct. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on-the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 32140, an anti-32140 antibody or its target molecule to facilitate separation of complexed from uncomplexed forms of one or both of the proteins, as well as to accommodate automation of the assay. Binding of a test compound to a 32140 protein, or interaction of a 32140 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/32140 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 32140 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 32140 binding or activity determined using standard techniques.

Other techniques for immobilizing either a 32140 protein or a target molecule on matrices include using conjugation of biotin and streptavidin. Biotinylated 32140 protein or target molecules can be prepared from biotin-NHS (N-hydroxy-succinimide) using techniques known in the art (e.g., biotinylation.kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 32140 protein or target molecules but which do not interfere with binding of the 32140 protein to its target molecule. Such antibodies can be derivatized to the wells of the plate, and unbound target or 32140 protein trapped in the wells by antibody conjugation. Methods for detecting such complexes, in addition to those described above for the GST-immobilized complexes, include immunodetection of complexes using antibodies reactive with the 32140 protein or target molecule, as well as enzyme-linked assays which rely on detecting an enzymatic activity associated with the 32140 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284–7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. Current Protocols in Molecular Biology 1999, J. Wiley: New York). Such resins and chromatographic techniques are known to one skilled in the art (see, e.g., Heegaard, N. H., (1998) *J. Mol. Recognit.* 11:141–8; Hage, D. S., and Tweed, S. A., (1997) *J. Chromatogr. B Biomed. Sci. Appl.* 699:499–525). Further, fluorescence energy transfer may also be conveniently utilized, as described herein, to detect binding without further purification of the complex from solution.

In a preferred embodiment, the assay includes contacting the 32140 protein or biologically active portion thereof with a known compound which binds 32140 to form an assay mixture, contacting the assay mixture with a test compound, and determining the ability of the test compound to interact with a 32140 protein, wherein determining the ability of the test compound to interact with a 32140 protein includes determining the ability of the test compound to preferentially bind to 32140 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." C.ompounds that disrupt such interactions can be useful in regulating the activity of the target gene product. Such compounds can include, but are not limited to molecules such as antibodies, peptides, and small molecules. The preferred target genes/products for use in this embodiment are the 32140 genes herein identified. In an alternative embodiment, the invention provides methods for determining the ability of the test compound to modulate the activity of a 32140 protein through modulation of the activity of a downstream effector of a 32140 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 32140 proteins can be used as "bait proteins" in a two-hybrid assay or three-hybrid assay (see, e.g., U.S. Pat. No. 5,283,317; Zervos et al., (1993) *Cell* 72:223–232; Madura et al., (1993) *J. Biol. Chem.* 268:12046–12054; Bartel et al., (1993) *Biotechniques* 14:920–924; Iwabuchi et al., (1993) *Oncogene* 8:1693–1696; and Brent WO94/10300), to identify other proteins, which bind to or interact with 32140 ("32140-binding proteins" or "32140-bp") and are involved in 32140 activity. Such 32140-bps can be activators or inhibitors of signals by the 32140 proteins or 32140 targets as, for example, downstream elements of a 32140-mediated signaling pathway.

The two-hybrid system is based on the modular nature of most transcription factors, which consist of separable DNA-binding and activation domains. Briefly, the assay utilizes two different DNA constructs. In one construct, the gene that codes for a 32140 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 32140 protein can be the fused to the activator domain.) If the "bait" and the "prey" proteins are able to interact, in vivo, forming a 32140-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 32140 protein.

In another embodiment, modulators of 32140 expression are identified. For example, a cell or cell free mixture is contacted with a candidate compound and the expression of 32140 mRNA or protein evaluated relative to the level of expression of 32140 mRNA or protein in the absence of the.candidate compound. When expression of 32140 mRNA or protein is greater in the presence of the candidate compound than in its absence, the candidate compound is identified as a stimulator of 32140 mRNA or protein expression. Alternatively, when expression of 32140 mRNA or protein is less (statistically significantly less) in the presence of the candidate compound than in its absence, the candidate compound is identified as an inhibitor of 32140 mRNA or protein expression. The level of 32140 mRNA or protein expression can be determined by methods described herein for detecting 32140 mRNA or protein.

In another aspect, the invention pertains to a combination of two or more of the assays described herein. For example, a modulating agent can be identified using a cell-based or a cell free assay, and the ability of the agent to modulate the activity of a 32140 protein can be confirmed in vivo, e.g., in an animal.

This invention further pertains to novel agents identified by the above-described screening assays. Accordingly, it is within the scope of this invention to further use an agent identified as described herein (e.g., a 32140 modulating agent, an antisense 32140 nucleic acid molecule, a 32140-specific antibody, or a 32140-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 32140 with a disease; (ii) identify an individual from a minute biological sample (tissue typing); and (iii) aid in forensic identification of a biological sample. These applications are described in the subsections below.

Chromosome Mapping

The 32140 nucleotide sequences or portions thereof can be used to map the location of the 32140 genes on a chromosome. This process is called chromosome mapping. Chromosome mapping is useful in correlating the 32140 sequences with genes associated with disease.

Briefly, 32140 genes can be mapped to chromosomes by preparing PCR primers (preferably 15–25 bp in length) from the 32140 nucleotide sequences. These primers can then be used for PCR screening of somatic cell hybrids containing individual human chromosomes. Only those hybrids containing the human gene corresponding to the 32140 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio P. et al., (1983) Science 220:919–924).

Other mapping strategies e.g., in situ hybridization (described in Fan, Y. et al., (1990) Proc. Natl. Acad. Sci. USA, 87:6223–27), pre-screening with labeled flow-sorted chromosomes, and pre-selection by hybridization to chromosome specific cDNA libraries can be used to map 32140 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al., (1987) Nature 325:783–787.

Moreover, differences in the DNA sequences between individuals affected and unaffected with a disease associated with the 32140 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 32140 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 32140 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 32140 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 32140 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e.

another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO: 1 having a length of at least 20 bases, preferably at least 30 bases) are particularly appropriate for this use.

The 32140 nucleotide sequences described herein can further be used to provide polynucleotide reagents, e.g., labeled or labelable probes which can be used in, for example, an in situ hybridization technique, to identify a specific tissue, e.g., a tissue containing aldehyde dehydrogenase activity. This can be very useful in cases where a forensic pathologist is presented with a tissue of unknown origin. Panels of such 32140 probes can be used to identify tissue by species and/or by organ type.

In a similar fashion, these reagents, e.g., 32140 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 32140.

Such disorders include, e.g., a disorder associated with the misexpression of 32140, or lipid metabolism related disorder.

The method includes one or more of the following:

detecting, in a tissue of the subject, the presence or absence of a mutation which affects the expression of the 32140 gene, or detecting the presence or absence of a mutation in a region which controls the expression of the gene, e.g., a mutation in the 5' control region;

detecting, in a tissue of the subject, the presence or absence of a mutation which alters the structure of the 32140 gene;

detecting, in a tissue of the subject, the misexpression of the 32140 gene, at the mRNA level, e.g., detecting a non-wild type level of a mRNA;

detecting, in a tissue of the subject, the misexpression of the gene, at the protein level, e.g., detecting a non-wild type level of a 32140 polypeptide.

In preferred embodiments the method includes: ascertaining the existence of at least one of: a deletion of one or more nucleotides from the 32140 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 naturally occurring mutants thereof or 5' or 3' flanking sequences naturally associated with the 32140 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 32140 gene; the presence of a non-wild type splicing pattern of a messenger RNA transcript of the gene; or a non-wild type level of 32140.

Methods of the invention can be used prenatally or to determine if a subject's offspring will be at risk for a disorder.

In preferred embodiments the method includes determining the structure of a 32140 gene, an abnormal structure being indicative of risk for the disorder.

In preferred embodiments the method includes contacting a sample form the subject with an antibody to the 32140 protein or a nucleic acid, which hybridizes specifically with the gene. These and other embodiments are discussed below.

Diagnostic and Prognostic Assays

The presence, level, or absence of 32140 protein or nucleic acid in a biological sample can be evaluated by obtaining a biological sample from a test subject and contacting the biological sample with a compound or an agent capable of detecting 32140 protein or nucleic acid (e.g., mRNA, genomic DNA) that encodes 32140 protein such that the presence of 32140 protein or nucleic acid is detected in the biological sample. The term "biological sample" includes tissues, cells and biological fluids isolated from a subject, as well as tissues, cells and fluids present within a subject. A preferred biological sample is serum. The level of expression of the 32140 gene can be measured in a number of ways, including, but not limited to: measuring the mRNA encoded by the 32140 genes; measuring the amount of protein encoded by the 32140 genes; or measuring the activity of the protein encoded by the 32140 genes.

The level of mRNA corresponding to the 32140 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated MRNA with a nucleic acid molecule (probe) that can hybridize to the mRNA encoded by the gene being detected. The nucleic acid probe can be, for example, a full-length 32140 nucleic acid, such as the nucleic acid of SEQ ID NO:1, or the DNA insert of the plasmid deposited with ATCC as Accession Number PTA-3424, or a portion thereof, such as an oligonucleotide of at least 7, 15, 30, 50, 100, 250 or 500 nucleotides in length and sufficient to specifically hybridize under stringent conditions to 32140 MRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 32140 genes.

The level of MRNA in a sample that is encoded by one of 32140 can be evaluated with nucleic acid amplification, e.g., by rtPCR (Mullis, 1987, U.S. Pat. No. 4,683,202), ligase chain reaction (Barany, 1991, *Proc. Natl. Acad. Sci. USA* 88:189–193), self sustained sequence replication (Guatelli et al., 1990, *Proc. Natl. Acad. Sci. USA* 87:1874–1878), transcriptional amplification system (Kwoh et al., 1989, *Proc.*

*Natl. Acad. Sci. USA* 86:1173–1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 32140 gene being analyzed.

In another embodiment, the methods further contacting a control sample with a compound or agent capable of detecting 32140 mRNA, or genomic DNA, and comparing the presence of 32140 mRNA or genomic DNA.in the control sample with the presence of 32140 mRNA or genomic DNA in the test sample.

A variety of methods can be used to determine the level of protein encoded by 32140. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 32140 protein in a biological sample in vitro as well as in vivo. In vitro techniques for detection of 32140 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 32140 protein include introducing into a subject a labeled anti-32140 antibody. For example, the antibody can be labeled with a radioactive marker whose presence and location in a subject can be detected by standard imaging techniques.

In another embodiment, the methods further include contacting the control sample with a compound or agent capable of detecting 32140 protein, and comparing the presence of 32140 protein in the control sample with the presence of 32140 protein in the test sample.

The invention also includes kits for detecting the presence of 32140 in a biological sample. For example, the kit can include a compound or agent capable of detecting 32140 protein or mRNA in a biological sample; and a standard. The compound or agent can be packaged in a suitable container. The kit can further comprise instructions for using the kit to detect 32140 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 32140 expression or activity. As used herein, the term "unwanted" includes an unwanted phenomenon involved in a biological response such as pain or deregulated cell proliferation.

In one embodiment, a disease or disorder associated with aberrant or unwanted 32140 expression or activity is identified. A test sample is obtained from a subject and 32140 protein or nucleic acid (e.g., mRNA or genomic DNA) is evaluated, wherein the level, e.g., the presence or absence, of 32140 protein or nucleic acid is diagnostic for a subject having or at risk of developing a disease or disorder associated with aberrant or unwanted 32140 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 32140 expression or activity. For example, such methods can be used to determine whether a subject can be effectively treated with an agent for an aldehyde oxidation related disorder.

The methods of the invention can also be used to detect genetic alterations in a 32140 gene, thereby determining if a subject with the altered gene is at risk for a disorder characterized by misregulation in 32140 protein activity or nucleic acid expression, such as an aldehyde oxidation disorder. In preferred embodiments, the methods include detecting, in a sample from the subject, the presence or absence of a genetic alteration characterized by at least one of an alteration affecting the integrity of a gene encoding a 32140-protein, or the misexpression of the 32140 gene. For example, such genetic alterations can be detected by ascertaining the existence of at least one of 1) a deletion of one or more nucleotides from a 32140 gene; 2) an addition of one or more. nucleotides to a 32140 gene; 3) a substitution of one or more nucleotides of a 32140 gene, 4) a chromosomal rearrangement of a 32140 gene; 5) an alteration in the level of a messenger RNA transcript of a 32140 gene, 6) aberrant modification of a 32140 gene, such as of the methylation pattern of the genomic DNA, 7) the presence of a non-wild type splicing pattern of a messenger RNA transcript of a 32140 gene, 8) a non-wild type level of a 32140-protein, 9) allelic loss of a 32140 gene, and 10) inappropriate post-translational modification of a 32140-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 32140-gene. This method can include the steps of collecting a sample of cells from a subject, isolating nucleic acid (e.g., genomic, mRNA or both) from the sample, contacting the nucleic acid sample with one or more primers which specifically hybridize to a 32140 gene under conditions such that hybridization and amplification of the 32140-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874–1878), transcriptional amplification system (Kwoh, D. Y. et al., (1989) *Proc. Natl. Acad. Sci. USA* 86:1173–1177), Q-Beta Replicase (Lizardi, P. M. et al., (1988) *Bio-Technology* 6:1197), or other nucleic acid amplification methods, followed by the detection of the amplified molecules using techniques known to those of skill in the art.

In another embodiment, mutations in a 32140 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for ihe presence of specific mutations by development or loss of a ribozyme cleavage site.

In other embodiments, genetic mutations in 32140 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin, M. T. et al., (1996) *Human Mutation* 7: 244–255; Kozal, M. J. et al., (1996) *Nature Medicine* 2:753–759). For example, genetic mutations in 32140 can be identified in two dimensional arrays containing light-generated DNA probes as described in Cronin, M. T. et al., supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 32140 gene and detect mutations by comparing the sequence of the sample 32140 with the corresponding wild-type (control) sequence. Automated sequencing procedures can be utilized when performing the diagnostic assays (Naeve et al., (1995) *Biotechniques* 19:448–453), including sequencing by mass spectrometry.

Other methods for detecting mutations in the 32140 gene include methods in which protection from cleavage agents is used to detect mismatched bases in RNA/RNA or RNA/DNA heteroduplexes (Myers et al., (1985) *Science* 230:1242–1246; Cotton et al., (1988) *Proc. Natl. Acad. Sci. USA* 85:4397–4401; Saleeba et al., (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 32140 cDNAs obtained from samples of cells. For example, the mutY enzyme of *E. coli* cleaves A at G/A mismatches and the thymidine DNA glycosylase from HeLa cells cleaves T at G/T mismatches (Hsu et al., (1994) *Carcinogenesis* 15:1657–1662; U.S. Pat. No. 5,459,039).

In other embodiments, alterations in electrophoretic mobility will be used to identify mutations in 32140 genes. For example, single strand conformation polymorphism (SSCP) may be used to detect differences in electrophoretic mobility between mutant and wild type nucleic acids (Orita et al., (1989) *Proc. Natl. Acad. Sci. USA:* 86:2766–2770, see also Cotton, (1993) *Mutat. Res.* 285:125–144; and Hayashi, (1992) *Genet. Anal. Tech. Appl.* 9:73–79). Single-stranded DNA fragments of sample and control 32140 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al., (1985) *Nature* 313:495–498). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner, (1987) *Biophys. Chem.* 265:12753).

Examples of other techniques for detecting point mutations include, but are not limited to, selective oligonucleotide hybridization, selective amplification, or selective primer extension (Saiki et al., (1986) *Nature* 324:163–166); Saiki et al., (1989) *Proc. Natl. Acad. Sci. USA* 86:6230–6234).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al., (1989) *Nucleic Acids Res.* 17:2437–2448) or at the extreme 3' end of one primer where, under appropriate conditions, mismatch can prevent, or reduce polymerase extension (Prossner, (1993) *Tibtech* 11:238). In addition it may be desirable to introduce a novel restriction site in the region of the mutation to create cleavage-based detection (Gasparini et al., (1992) *Mol. Cell Probes* 6:1–7). It is anticipated that in certain embodiments amplification may also be performed using Taq ligase for amplification (Barany, (1991) *Proc. Natl. Acad. Sci USA* 88:189–193). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 32140 gene.

Use of 32140 Molecules as Surrogate Markers

The 32140 molecules of the invention are also useful as markers of disorders or disease states, as. markers for precursors of disease states, as markers for predisposition of disease states, as markers of drug activity, or as markers of the pharmacogenomic profile of a subject. Using the methods described herein, the presence, absence and/or quantity of the 32140 molecules of the invention may be detected, and may be correlated with one or more biological states in vivo. For example, the 32140 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al., (2000) *J. Mass. Spectrom.* 35: 258–264; and James, (1994) *AIDS Treatment News Archive* 209.

The 32140 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 32140 marker) transcription or expression, the amplified marker may be in a quantity which is more readily detectable than the drug itself. Also, the marker may be more easily detected due to the nature of the marker itself; for example, using the methods described herein, anti-32140 antibodies may be employed in an immune-based detection system for a 32140 protein marker, or 32140-specific radiolabeled probes may be used to detect a 32140 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90: 229–238; Schentag (1999) *Am. J. Health-Syst. Pharm.* 56 Suppl. 3: S21–S24; and Nicolau (1999) *Am, J. Health-Syst. Pharm.* 56 Suppl. 3: S16–S20.

The 32140 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 32140 protein or RNA) for specific tumor markers in a subject, a drug or course of treatment may be selected that is optimized for the treatment of the specific tumor likely to be present in the subject. Similarly, the presence or absence of a specific sequence mutation in 32140 DNA may correlate 32140 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-32140 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsipp any, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compQunds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. The antibodies produced, that bind to the polypeptides encoded by SEQ ID NO:1 or SEQ ID NO:3 or encoded by nucleotide sequences that are 60% identical to SEQ ID NO:1 or SEQ ID NO:3, can be used to treat disorders in a patient involving the lung, liver, brain, heart, kidney, breast, and testis. More specifically, the antibodies can be used to treat viral disorders including but not limited to Herpes Simplex Virus.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al., ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 gram s per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about Imicrogram per kilogram to about 500 milligrams per kilogram, about 100 micrograms per kilogram to about 5 milligrams per kilogram, or about Imicrogram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al., (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment:

The present invention provides for both prophylactic and therapeutic methods of treating a subject at risk of (or susceptible to) a disorder or having. a disorder associated with aberrant or unwanted 32140 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 32140 molecules of the present invention or 32140 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 32140 expression or activity, by administering to the subject a 32140 or an agent which modulates 32140 expression or at least one 32140 activity. Subjects at risk for a disease which is caused or contributed to by aberrant or unwanted 32140 expression or activity can be identified by, for example, any or a combination of diagnostic or prognostic assays as described herein. Administration of a prophylactic agent can occur prior to the manifestation of symptoms characteristic of the 32140 aberrance, such that a disease or disorder is prevented or, alternatively, delayed in its progression. Depending on the type of 32140 aberrance, for example, a 32140, 32140 agonist or 32140 antagonist agent can be used for treating the subject. The appropriate agent can be determined based on screening assays described herein.

It is possible that some 32140 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 32140 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 32140 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the. target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity. Thus, ribozymes and antisense molecules may be used to treat disorders in a patient involving lung, liver, brain, heart, kidney, breast, and testis. Also, ribozymes may be used to treat viral disorders in a patient including but not limited to Herpes Simplex Virus.

Another method by which nucleic acid molecules may be utilized in treating or preventing a disease characterized by 32140 expression is through the use of aptamer molecules specific for 32140 protein. Aptamers are nucleic acid molecules having a tertiary structure which permits them to specifically bind to protein ligands (see, e.g., Osborne, et al., *Curr. Opin. Chem. Biol.* 1997, 1: 5–9; and Patel, D. J., *Curr. Opin. Chem. Biol.* 1997 Jun; 1:32–46). Since nucleic acid molecules may in many cases be more conveniently introduced into target cells than therapeutic protein molecules may be, aptamers offer a method by which 32140 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 32140 disorders. For a description of antibodies, see the Antibody section above.

In circumstances wherein injection of an animal or a human subject with a 32140 protein or epitope for stimulating antibody production is harmful to the subject, it is possible to generate an immune response against 32140 through the use of anti-idiotypic antibodies (see, for example, Herlyn, D., (1999) *Ann. Med.* 31(1):66–78; and Bhattacharya-Chatte jee, M., and Foon, K. A., (1998) *Cancer Treat. Res.* 94:51–68). If an anti-idiotypic antibody is introduced into a mammal or human subject, it should stimulate the production of anti-anti-idiotypic antibodies, which should be specific to the 32140 protein. Vaccines directed to a disease characterized by 32140 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al., (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 32140 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 32140 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell, R. J. et al., (1996) *Curr. Opin. Biotechnol.* 7:89–94 and in Shea, K. J., (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis, G. et al., (1993) *Nature* 361:645–647. Through the use of isotope-labeling, the "free" concentration of compound which modulates the expression or activity of 32140 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz, D. et al., (1995) *Anal. Chem.* 67:2142–2144.

Another aspect of the invention pertains to methods of modulating 32140 expression or activity for therapeutic purposes. Accordingly, in an exemplary embodiment, the modulatory method of the invention involves contacting a cell with a 32140 or agent that modulates one or more of the activities of 32140 protein activity associated with the cell. An agent that modulates 32140 protein activity can be an agent as described herein, such as a nucleic acid or a protein, a naturally-occurring target molecule of a 32140 protein (e.g., a 32140 substrate or receptor), a 32140 antibody, a 32140 agonist or antagonist, a peptidomimetic of a 32140 agonist or antagonist, or other small molecule.

In one embodiment, the agent stimulates one or 32140 activities. Examples of such stimulatory agents include active 32140 protein and a nucleic acid molecule encoding 32140. In another embodiment, the agent inhibits one or more 32140 activities. Examples of such inhibitory agents include antisense 32140 nucleic acid molecules, anti-32140 antibodies, and 32140inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 32140 protein or nucleic acid molecule. In one embodiment, the method involves administering an agent (e.g., an agent identified by a screening assay described herein), or combination of agents that modulates (e.g., upregulates or downregulates) 32140 expression or activity. In another embodiment, the method involves administering a 32140 protein or nucleic acid molecule as therapy to compensate for reduced, aberrant, or unwanted 32140 expression or activity.

Stimulation of 32140 activity is desirable in situations in which 32140 is abnormally downregulated and/or in which increased 32140 activity is likely to have a beneficial effect. For example, stimulation of 32140 activity is desirable in situations in which a 32140 is downregulated and/or in which increased 32140 activity is likely to have a beneficial effect. Likewise, inhibition of 32140 activity is desirable in situations in which 32140 is abnormally upregulated and/or in which decreased 32140 activity is likely to have a beneficial effect.

The 32140 molecules can act as novel diagnostic targets and therapeutic agents for controlling one or more aldehyde oxidation-related disorders, including cellular proliferative and/or differentiative disorders, cardiovascular disorders, as described above, as well as disorders associated with or metabolic disorders.

Aberrant expression and/or activity of 32140 molecules may mediate disorders associated with bone metabolism. "Bone metabolism" refers to direct or indirect effects in the formation or degeneration of bone structures, e.g., bone formation, bone resorption, etc., which may ultimately affect the concentrations in serum of calcium and phosphate. This term also includes activities mediated by 32140 molecules effects in bone cells, e.g. osteoclasts and osteoblasts, that may in turn result in bone formation and degeneration. For example, 32140 molecules may support different activities of bone resorbing osteoclasts such as the stimulation of differentiation of monocytes and mononuclear phagocytes into osteoclasts. Accordingly, 32140 molecules that modulate the production of bone cells can influence bone formation and degeneration, and thus may be used to treat bone disorders. Examples of such disorders include, but are not limited to, osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, rickets, sarcoidosis, glucocorticoid antagonism, malabsorption syndrome, steatorrhea, tropical sprue, idiopathic hypercalcemia and milk fever.

Examples of hematopoietic disorders include, but are not limited to, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Disorders which may be treated or diagnosed by methods described herein include, but are not limited to, disorders associated with an accumulation in the liver of fibrous tissue, such as that resulting from an imbalance between production and degradation of the extracellular matrix accompanied by the collapse and condensation of preexisting fibers. The methods described herein can be used to diagnose or treat hepatocellular necrosis or injury induced by a wide variety of agents including processes which disturb homeostasis, such as an inflammatory process, tissue damage resulting from toxic injury or altered hepatic blood flow, and infections (e.g., bacterial, viral and parasitic). For example, the methods can be used for the early detection of hepatic injury, such as portal hypertension or hepatic fibrosis. In addition, the methods can be employed to detect liver fibrosis attributed to inborn errors of metabolism, for example, fibrosis resulting from a storage disorder such as Gaucher's disease (lipid abnormalities) or a glycogen storage disease, A1-antitrypsin deficiency; a disorder mediating the accumulation (e g., storage) of an exogenous substance, for example, hemochromatosis (iron-overload syndrome) and copper storage diseases (Wilson's disease), disorders resulting in the accumulation of a toxic metabolite (e.g., tyrosinemia, fructosemia and galactosemia) and peroxisomal disorders (e.g., Zellweger syndrome). Additionally, the methods described herein may be useful for the early detection and treatment of liver injury associated with the administration of various chemicals or drugs, such as for example, methotrexate, isonizaid, oxyphenisatin, methyldopa, chlorpromazine, tolbutamide or alcohol, or which represents a hepatic manifestation of a vascular disorder such as obstruction of either the intrahepatic or extrahepatic bile flow or an alteration in hepatic circulation resulting, for example, from chronic heart failure, veno-occlusive disease, portal vein thrombosis or Budd-Chiari syndrome.

Additionally, 32140 molecules may play an important role in the etiology of certain viral diseases, including but not limited to, Hepatitis B, Hepatitis C and Herpes Simplex Virus (HSV). Modulators of 32140 activity could be used to control viral diseases. The modulators can be used in the treatment and/or diagnosis of viral infected tissue or virus-associated tissue fibrosis, especially liver and liver fibrosis. Also, 32140 modulators can be used in the treatment and/or diagnosis of virus-associated carcinoma, especially hepatocellular cancer.

Additionally, 32140 may play an important role in the regulation of metabolism or pain disorders. Diseases of metabolic imbalance include, but are not limited to, obesity, anorexia nervosa, cachexia, lipid disorders, and diabetes. Examples of pain disorders include, but are not limited to, pain response elicited during various forms of tissue injury, e.g., inflammation, infection, and ischemia, usually referred to as hyperalgesia (described in, for example, Fields, H. L., (1987) *Pain*, New York: McGraw-Hill); pain associated with musculoskeletal disorders, e.g., joint pain; tooth pain; headaches; pain associated with surgery; pain related to irritable bowel syndrome; or chest pain.

Pharmacogenomics

The 32140 molecules of the present invention, as well as agents, or modulators which have a stimulatory or inhibitory effect on 32140 activity (e.g., 32140 gene expression) as identified by a screening assay described herein can be administered to individuals to treat (prophylactically or therapeutically) 32140 associated disorders (e.g., cellular growth related disorders) associated with aberrant or unwanted 32140 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 32140 molecule or 32140 modulator as well as tailoring the dosage and/or therapeutic regimen of treatment with a 32140 molecule or 32140 modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23:983–985 and Linder, M. W. et al. (1997) *Clin. Chem.* 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 32140 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 32140 molecule or 32140 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 32140 molecule or 32140 modulator, such as a modulator identified by one of the exemplary screening assays described herein.

The present invention further provides methods for identifying new agents, or combinations, that are based on identifying agents that modulate the activity of one or more of the gene products encoded by one or more of the 32140 genes of the present invention, wherein these products may be associated with resistance of the cells to a therapeutic agent. Specifically, the activity of the proteins encoded by the 32140 genes of the present invention can be used as a basis for identifying agents for overcoming agent resistance. By blocking the activity of one or more of the resistance proteins, target cells, e.g., cancer cells, will become sensitive to treatment with an agent that the unmodified target cells were resistant to.

Monitoring the influence of agents (e.g., drugs) on the expression or activity of a 32140 protein can be applied in clinical trials. For example, the effectiveness of an agent determined by a screening assay as described herein to increase 32140 gene expression, protein levels, or upregulate 32140 activity, can be monitored in clinical trials of subjects exhibiting decreased 32140 gene expression, protein levels, or downregulated 32140 activity. Alternatively, the effectiveness of an agent determined by a screening assay to decrease 32140 gene expression, protein levels, or downregulate 32140 activity, can be monitored in clinical trials of subjects exhibiting increased 32140 gene expression, protein levels, or upregulated 32140 activity. In such clinical trials, the expression or activity of a 32140 gene, and preferably, other genes that have been implicated in, for example, a 32140-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 32140, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 32140 nucleic acid, polypeptide, or antibody.

The capture probes can be a set of nucleic acids from a selected sample, e.g., a sample of nucleic acids derived from a control or non-stimulated tissue or cell.

The method can include contacting the 32140 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 32140. Such methods can be used to diagnose a subject, e.g., to evaluate risk for a disease or disorder, to evaluate suitability of a selected treatment for a subject, to evaluate whether a subject has a disease or disorder. 32140 is associated with aldehyde dehydrogenase activity, thus it is useful for disorders associated with abnormal lipid metabolism.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 32140 or from a cell or subject in which a 32140 mediated response has been elicited, e.g., by contact of the cell with 32140 nucleic acid or protein, or administration to the cell or subject 32140 nucleic acid or protein; contacting the array with one or more inquiry probe, wherein an inquiry probe can be a nucleic acid, polypeptide, or antibody (which is preferably other than 32140 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 32140 (or does not express as highly as in the case of the 32140 positive plurality of capture probes) or from a cell or subject which in which a 32140 mediated response has not been elicited (or has been elicited to a lesser extent than in the first sample); contacting the array with one or more inquiry probes (which is preferably other than a 32140 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 32140, e.g., analyzing structure, function, or relatedness to other nucleic acid or amino acid sequences. The method includes: providing a 32140 nucleic acid or amino acid sequence; comparing the 32140 sequence with one or more preferably a plurality of sequences from a collection of sequences, e.g., a nucleic acid or protein sequence database; to thereby analyze 32140.

Preferred databases include GenBank™. The method can include evaluating the sequence identity between a 32140 sequence and a database sequence. The method can be performed by accessing the database at a second site, e.g., over the internet.

In another aspect, the invention features, a set of oligonucleotides, useful, e.g., for identifying SNP's, or identifying specific alleles of 32140. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1
Identification and Characterization of Human 32140 cDNAs

The human 32140 sequence (FIG. 1A–B; SEQ ID NO:1), which is approximately 7220 nucleotides long including untranslated regions, contains a predicted methionine-initiated coding sequence of about 2769 nucleotides (nucleotides 129–2897 of SEQ ID NO: 1; SEQ ID NO:3), excluding the terminal codon. The coding sequence encodes a 923 amino acid protein (SEQ ID NO:2).

Example 2
Tissue Distribution of 32140 mRNA

Northern blot hybridizations with various RNA samples can be performed under standard conditions and washed under stringent conditions, i.e., 0.2×SSC at 65° C. A DNA probe corresponding to all or a portion of the 32140 cDNA. (SEQ ID NO:1). The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

Example 3
Recombinant Expression of 32140 in Bacterial Cells

In this example, 32140 is expressed as a recombinant glutathione-S-transferase (GST) fusion polypeptide in *E. coli* and the fusion polypeptide is isolated and characterized. Specifically, 32140 is fuised to GST and this fuision polypeptide is expressed in *E. coli*, e.g., strain PEB199. Expression of the GST-32140 fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 4
Expression of Recombinant 32140 Protein in COS Cells

To express the 32140 gene in COS cells, the pcDNA/Amp vector by Invitrogen Corporation (San Diego, CA) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 32140 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 32140 DNA sequence is amplified by PCR using two primers. The 5' primer contains the restriction site of interest followed by approximately twenty nucleotides of the 32140 coding sequence starting from the initiation codon; the 3' end sequence contains complementary sequences to the other restriction site of interest, a translation stop codon, the HA tag or FLAG tag and the last 20 nucleotides of the 32140 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 32140 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 32140-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989. The expression of the 32140 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 32140 coding sequence is cloned directly into the polyliriker of the pCDNA/Amp vector using the appropriate restriction sites. The resulting plasmid is transfected into COS cells in the manner described above, and the expression of the 32140 polypeptide is detected by radiolabelling and immunoprecipitation using a 32140 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
<160> NUMBER OF SEQ ID NOS: 4

<210> SEQ ID NO 1
<211> LENGTH: 7220
<212> TYPE: DNA
<213> ORGANISM: Homo sapiens
<220> FEATURE:
<221> NAME/KEY: CDS
<222> LOCATION: (129)...(2900)

<400> SEQUENCE: 1
agcggcgagc cgcgaaccag gcagtccggg gcatccagac tgcaggccgc gcccaggccg        60
cgcccaggct gcgccgcccg cctgcctccc gcgctgccgc gtcgccagtg ctagcgctcc       120 tctccagc atg ctg cgg cgg ggc agc cag gcg ctc cgg cgc ttc tcc act       170
         Met Leu Arg Arg Gly Ser Gln Ala Leu Arg Arg Phe Ser Thr
          1               5                  10 ggc cgg gtt tat ttc aaa aac aag ctg aag ttg gca cta att ggc cag       218
Gly Arg Val Tyr Phe Lys Asn Lys Leu Lys Leu Ala Leu Ile Gly Gln
 15                  20                  25                  30 agc ctc ttt gga caa gaa gtc tat agc cac ctc cgc aaa gag ggc cac       266
Ser Leu Phe Gly Gln Glu Val Tyr Ser His Leu Arg Lys Glu Gly His
                 35                  40                  45 cga gta gta ggg gtg ttc aca gtt cca gac aag gat gga aaa gct gac       314
Arg Val Val Gly Val Phe Thr Val Pro Asp Lys Asp Gly Lys Ala Asp
             50                  55                  60 cct ctg gct ttg gct gca gag aaa gat ggg acc cct gtg ttc aag ctt       362
Pro Leu Ala Leu Ala Ala Glu Lys Asp Gly Thr Pro Val Phe Lys Leu
 65                  70                  75 cct aaa tgg agg gtc aag ggc aag acc atc aaa gaa gtg gca gaa gcc       410
Pro Lys Trp Arg Val Lys Gly Lys Thr Ile Lys Glu Val Ala Glu Ala
 80                  85                  90 tac aga tcc gtg ggt gca gag cta aat gtg ctc cct ttc tgc act cag       458
Tyr Arg Ser Val Gly Ala Glu Leu Asn Val Leu Pro Phe Cys Thr Gln
 95                  100                 105                 110 ttc att ccc atg gat ata att gat agt cca aag cac ggc tct atc att       506
Phe Ile Pro Met Asp Ile Ile Asp Ser Pro Lys His Gly Ser Ile Ile
                 115                 120                 125 tat cac cca tcc atc ctg ccc agg cac aga gga gcc tct gct atc aat       554
Tyr His Pro Ser Ile Leu Pro Arg His Arg Gly Ala Ser Ala Ile Asn
             130                 135                 140
```

```
tgg act cta att atg gga gat aag aaa gct ggg ttt tct gtt ttc tgg      602
Trp Thr Leu Ile Met Gly Asp Lys Lys Ala Gly Phe Ser Val Phe Trp
        145                 150                 155 gct gat gat ggc ttg gat aca gga ccc atc ctt ctt cag aga tca tgt      650
Ala Asp Asp Gly Leu Asp Thr Gly Pro Ile Leu Leu Gln Arg Ser Cys
    160                 165                 170 gat gtt gaa ccc aat gat aca gtg gat gca ctt tat aat cgg ttt ctt      698
Asp Val Glu Pro Asn Asp Thr Val Asp Ala Leu Tyr Asn Arg Phe Leu
175                 180                 185                 190 ttt cct gaa gga atc aag gcc atg gta gaa gct gtc caa ctc ata gct      746
Phe Pro Glu Gly Ile Lys Ala Met Val Glu Ala Val Gln Leu Ile Ala
                195                 200                 205 gat gga aaa gct cct cgt ata ccc cag cca gaa gaa ggg gca aca tat      794
Asp Gly Lys Ala Pro Arg Ile Pro Gln Pro Glu Glu Gly Ala Thr Tyr
        210                 215                 220 gaa ggt atc cag aaa aag gaa aat gct gag att tct tgg gac cag tct      842
Glu Gly Ile Gln Lys Lys Glu Asn Ala Glu Ile Ser Trp Asp Gln Ser
    225                 230                 235 gcc gaa gtt tta cat aac tgg att cga ggt cat gat aaa gtc cct gga      890
Ala Glu Val Leu His Asn Trp Ile Arg Gly His Asp Lys Val Pro Gly
240                 245                 250 gct tgg aca gag ata aat gga cag atg gtc act ttc tat ggc tcg aca      938
Ala Trp Thr Glu Ile Asn Gly Gln Met Val Thr Phe Tyr Gly Ser Thr
255                 260                 265                 270 tta ctg aat agc tct gtg cct cct gga gaa cca ctg gaa att aaa ggt      986
Leu Leu Asn Ser Ser Val Pro Pro Gly Glu Pro Leu Glu Ile Lys Gly
                275                 280                 285 gcc aag aag cct ggt ctc gtt acc aaa aat gga ctt gtt ctt ttt ggt     1034
Ala Lys Lys Pro Gly Leu Val Thr Lys Asn Gly Leu Val Leu Phe Gly
        290                 295                 300 aac gat gga aaa gca ctg acg gtg aga aat ctg cag ttt gaa gat gga     1082
Asn Asp Gly Lys Ala Leu Thr Val Arg Asn Leu Gln Phe Glu Asp Gly
    305                 310                 315 aaa atg atc cct gcc tct cag tac ttt tca acg ggt gag acg tca gtg     1130
Lys Met Ile Pro Ala Ser Gln Tyr Phe Ser Thr Gly Glu Thr Ser Val
320                 325                 330 gta gaa ctg aca gct gaa gag gtg aaa gtg gca gag acc atc aag gtc     1178
Val Glu Leu Thr Ala Glu Glu Val Lys Val Ala Glu Thr Ile Lys Val
335                 340                 345                 350 atc tgg gct gga att tta agc aat gtc ccc att att gaa gac tca aca     1226
Ile Trp Ala Gly Ile Leu Ser Asn Val Pro Ile Ile Glu Asp Ser Thr
                355                 360                 365 gac ttc ttt aaa tct gga gca agc tca atg gat gtt gcc agg ctg gtt     1274
Asp Phe Phe Lys Ser Gly Ala Ser Ser Met Asp Val Ala Arg Leu Val
        370                 375                 380 gaa gag atc aga cag aaa tgt ggt ggg ctt cag ttg cag aat gaa gat     1322
Glu Glu Ile Arg Gln Lys Cys Gly Gly Leu Gln Leu Gln Asn Glu Asp
    385                 390                 395 gtc tat atg gcc acc aag ttt gaa ggc ttt atc caa aag gtc gtg agg     1370
Val Tyr Met Ala Thr Lys Phe Glu Gly Phe Ile Gln Lys Val Val Arg
400                 405                 410 aaa ctg aga gga gaa gat caa gag gtg gag ctg gtt gta gat tat att     1418
Lys Leu Arg Gly Glu Asp Gln Glu Val Glu Leu Val Val Asp Tyr Ile
415                 420                 425                 430 tca aag gag gtc aat gaa atc atg gta aaa atg cca tac cag tgt ttc     1466
Ser Lys Glu Val Asn Glu Ile Met Val Lys Met Pro Tyr Gln Cys Phe
                435                 440                 445 ata aat gga cag ttc aca gat gca gac gat gga aag act tac gac act     1514
Ile Asn Gly Gln Phe Thr Asp Ala Asp Asp Gly Lys Thr Tyr Asp Thr
        450                 455                 460
```

```
atc aac cca aca gat gga tct aca ata tgc aaa gta tcc tac gct tct    1562
Ile Asn Pro Thr Asp Gly Ser Thr Ile Cys Lys Val Ser Tyr Ala Ser
        465                 470                 475 ttg gcg gat gtt gat aaa gca gta gca gca gca aaa gat gct ttt gaa    1610
Leu Ala Asp Val Asp Lys Ala Val Ala Ala Ala Lys Asp Ala Phe Glu
        480                 485                 490 aac ggt gaa tgg gga aga atg aat gca aga gaa aga gga aga ttg atg    1658
Asn Gly Glu Trp Gly Arg Met Asn Ala Arg Glu Arg Gly Arg Leu Met
495                 500                 505                 510 tat aga ctt gca gac cta ctg gaa gag aac caa gaa gag ctg gca act    1706
Tyr Arg Leu Ala Asp Leu Leu Glu Glu Asn Gln Glu Glu Leu Ala Thr
                515                 520                 525 att gaa gcc ctt gat tca ggg gct gtc tat acc ttg gcc ctg aag aca    1754
Ile Glu Ala Leu Asp Ser Gly Ala Val Tyr Thr Leu Ala Leu Lys Thr
            530                 535                 540 cac att gga atg tct gtg caa aca ttc aga tat ttt gct ggc tgg tgc    1802
His Ile Gly Met Ser Val Gln Thr Phe Arg Tyr Phe Ala Gly Trp Cys
        545                 550                 555 gac aaa att cag ggt tct act att cca atc aac cag gcc cgt cca aat    1850
Asp Lys Ile Gln Gly Ser Thr Ile Pro Ile Asn Gln Ala Arg Pro Asn
        560                 565                 570 cgc aat ctg acc ttc acc aag aaa gag cca ctc ggt gtc tgt gcc att    1898
Arg Asn Leu Thr Phe Thr Lys Lys Glu Pro Leu Gly Val Cys Ala Ile
575                 580                 585                 590 att att ccc tgg aac tac ccg ctg atg atg ctg gca tgg aag agt gct    1946
Ile Ile Pro Trp Asn Tyr Pro Leu Met Met Leu Ala Trp Lys Ser Ala
                595                 600                 605 gcg tgt ttg gca gca ggc aat acc tta gtg ctc aag cca gca cag gtc    1994
Ala Cys Leu Ala Ala Gly Asn Thr Leu Val Leu Lys Pro Ala Gln Val
            610                 615                 620 acg ccc ttg act gct ttg aag ttt gca gaa ctg tct gtg aaa gca ggc    2042
Thr Pro Leu Thr Ala Leu Lys Phe Ala Glu Leu Ser Val Lys Ala Gly
        625                 630                 635 ttt cca aag ggg gtc atc aac atc att cca ggc tca ggt ggc ata gca    2090
Phe Pro Lys Gly Val Ile Asn Ile Ile Pro Gly Ser Gly Gly Ile Ala
        640                 645                 650 gga caa cgt ctg tct gaa cat cct gac atc cgc aaa ctt ggt ttc act    2138
Gly Gln Arg Leu Ser Glu His Pro Asp Ile Arg Lys Leu Gly Phe Thr
655                 660                 665                 670 gga tcc act cct att ggc aaa cag atc atg aag agc tgt gct gtt agc    2186
Gly Ser Thr Pro Ile Gly Lys Gln Ile Met Lys Ser Cys Ala Val Ser
                675                 680                 685 aac ttg aag aaa gtt tcc ctt gag ctt ggt ggc aag tct cca ctt ata    2234
Asn Leu Lys Lys Val Ser Leu Glu Leu Gly Gly Lys Ser Pro Leu Ile
            690                 695                 700 ata ttt aat gac tgt gaa ctt gac aag gct gtg cga atg ggc atg gga    2282
Ile Phe Asn Asp Cys Glu Leu Asp Lys Ala Val Arg Met Gly Met Gly
        705                 710                 715 gca gta ttt ttc aac aaa gga gag aac tgt att gct gct ggg cgg ttg    2330
Ala Val Phe Phe Asn Lys Gly Glu Asn Cys Ile Ala Ala Gly Arg Leu
        720                 725                 730 ttc gtg gaa gaa tcc atc cac gac gaa ttt gtg aca aga gtg gta gaa    2378
Phe Val Glu Glu Ser Ile His Asp Glu Phe Val Thr Arg Val Val Glu
735                 740                 745                 750 gaa att aaa aag atg aaa att ggt gat cca ctt gac aga tcc act gat    2426
Glu Ile Lys Lys Met Lys Ile Gly Asp Pro Leu Asp Arg Ser Thr Asp
                755                 760                 765 cat ggg ccc caa aat cat aag gct cat ctg gaa aag ctg ctg caa tac    2474
His Gly Pro Gln Asn His Lys Ala His Leu Glu Lys Leu Leu Gln Tyr
```

```
                    770              775              780
tgt gaa act gga gtg aaa gaa ggg gcc act ttg gtg tac ggg gga aga       2522
Cys Glu Thr Gly Val Lys Glu Gly Ala Thr Leu Val Tyr Gly Gly Arg
            785              790              795 caa gtc caa agg cca ggc ttt ttc atg gag ccg acc gtg ttc aca gat       2570
Gln Val Gln Arg Pro Gly Phe Phe Met Glu Pro Thr Val Phe Thr Asp
    800              805              810 gtg gaa gac tac atg tac ctc gcc aaa gag gaa tcc ttt ggg cct att       2618
Val Glu Asp Tyr Met Tyr Leu Ala Lys Glu Glu Ser Phe Gly Pro Ile
815              820              825              830 atg gtc att tct aaa ttc caa aat ggg gac atc gat gga gtg ttg cag       2666
Met Val Ile Ser Lys Phe Gln Asn Gly Asp Ile Asp Gly Val Leu Gln
                835              840              845 cga gca aat agt aca gag tat ggt ttg gcc tca ggg gtt ttt aca aga       2714
Arg Ala Asn Ser Thr Glu Tyr Gly Leu Ala Ser Gly Val Phe Thr Arg
            850              855              860 gac ata aac aaa gct atg tat gtg agt gaa aaa ctg gaa gca gga act       2762
Asp Ile Asn Lys Ala Met Tyr Val Ser Glu Lys Leu Glu Ala Gly Thr
        865              870              875 gtt ttt att aac aca tac aac aag aca gat gtg gcg gcc cca ttt ggc       2810
Val Phe Ile Asn Thr Tyr Asn Lys Thr Asp Val Ala Ala Pro Phe Gly
880              885              890 gga gtt aaa caa tct ggc ttt gga aaa gac tta ggt gag gaa gct cta       2858
Gly Val Lys Gln Ser Gly Phe Gly Lys Asp Leu Gly Glu Glu Ala Leu
895              900              905              910 aat gaa tat ctc aaa acc aag acg gtg aca ctg gaa tat tag              2900
Asn Glu Tyr Leu Lys Thr Lys Thr Val Thr Leu Glu Tyr  *
                915              920 agcaacacca tcatcaggaa agccttgaca gacagccctt tacaactctg acacactta     2960 agaagattgg gtgtgttgag gcaggaggtg tcagccacaa accaaaaaat acacagatgg    3020
accatgaaga gggccaggcc atgttaaagc atttacacat gtgcctgagt attttctaat    3080
acaccttcca gtgatttgga gttgttgcat tttgactatg ttgtatatca tacgtatttc    3140
taaaatacca agctgtttct cccctaccta gacaaatcta ttcatggttc ccatcttgaa    3200
gatgtcagta ccatgcagtt ataatacaca aggtgcattt attggaaact tgtataata    3260 tgtacaggtt tttaacctct gaactataca taggggggtta ttaaaaagat tttctataag  3320
tcttctaagg aacagtataa cctgtaagga atgtgaaggt agttcttttt tagtatttgg   3380
aaataagata catctttgtg cctttgatat tccattttt aacccactgt gatgggtgat    3440
caacctagaa acattatctt gagtacctac taggtaccag gtactatatt atgttctgag   3500
gagtatagag aatttaatga tatgatggct ggcccccaca tagtttaaat tttagtaaat   3560
agcttttgaa gcaaatttta catatgatat agtagaaggc tgatccctgg tcgtatcata   3620
ccatcttcct atctatgtaa ctttgggaaa ctctcgcaac tcctctgagc ctctgcttcc   3680
ctatgtgtaa aacagggata gtaaatgcct tcctcaggac ccttaatagg agaattcatt   3740
gcagtaatgt aagtaaagca cctcacatta atgctttgct catggtaagt actcaaattt   3800
aactctgatt tcctccgtca ccattcttaa aagatattga gatagtttaa ttaactagat   3860
gaattcattt cccacaaccc ttttcaatca tcaattccta gatattttc tcatccattg    3920 ttctgacaca atgcctgata cagcagcact gaaaaatgcc acacaatgaa aaatggcaat   3980
agtacaagga aaaggggtgc ttttctttgg gcagctcgct cgtccttcat gggacatctt   4040
actttccatt tttctaccta ttggttctgc tgttcactgg ctgtgtgatc ttgggcaaga   4100
tagtaatcta atatctcaga gcctaggttg agtatctata aaatgaaaat caaatctcta   4160
```

-continued

```
tctcagtagg tgttgcaagg attcagtgag ataatataca taatgcactt aacaaggcgt    4220
ttggaccata gcattgaaga aatggaaact attaacagcc catttcccat tggcagacag    4280
aagtagtcag gtgagtaaat tttcaccatc tatgtgtgac tagaaggcgg caaatttctg    4340
aatcacatga gtctccaaaa gatagccaga aagttaaatt ctattaatcc tcctttaaaa    4400
ataaaatttc agtaaacatt ccttttttctt tggctttgaa gaagccttag ggaatatttg    4460
tcattttgga gacttggcag aataacatga ggggattgta gggaatcaat aaaaactaaa    4520
caacaaaatc agagtcagag aacattttca aaaggaagaa taggaggttt gatcccagca    4580
tgataaacag agcgaatttg gcctggaagc acttttgatt atactatagc tcatttacca    4640
tcccagagtt tggcacagct gaaattttaa gttggaatga atattcactg ggcccaaaat    4700
gacagttcat atttgaataa aagtgacaaa agccttttta taagtaatca cttttaagtg    4760
aaatgtttta actgatttca tgtgatttag aatatgattt aatcaaatta ttttaatgat    4820
agatggaatg gcagacaaaa acatgcctgt ccttctagac tgattttact ttaccctcta    4880
atattcatct cagtagcagt gttttaaata ttctctgggc tgcaaaactc tttgggaatc    4940
tgataaaagc tatgaacact ccctgtgtcc cgcttctacc cccaaaattc atgtgcacac    5000
acacaattct gcaagtatct tcaaagggtt cacagacctc ccaaaggcca tgcttgggcc    5060
ccagattaag aactcctttc tccatagcaa gttttaaaca tttcttacca gcttacattt    5120
ttagatctgg ctgatcagaa tcaaaggctc tgtgtaatac ataaagttac caagtgaact    5180
ggaattggaa catcaccctc cccagcctgc taggtgattt acttaacaca tagagtaata    5240
aaatcatcgc tgttgcttta gatcacggat tattttgcta ataatgctaa ggatgaagct    5300
gtgatcttat tatcacctga atcgggaggt gtggacactt taagcagttc cactttcctt    5360
ctaattcccc atccccatgc ctttgctaaa gctgtccctt tgctctaac accccttcctg    5420
gaccttccta ccctagctgg gctaagtgtt tctcctcagc gttcccactt gtttcaaaca    5480
tagcacttac cacttgtact aaaattactt gccttcttaa ttagatatga acaaccctcc    5540
ccaactccag tatgggcctt ctgtcaataa taatacgata tgacagctac catttattaa    5600
gggcctcctg tatgaaagac cttaggctaa gcatgtttta aatgttattt aatcttcaca    5660
atctctgaaa aaaatgaaga aatcaacgtg cttttcttac tacctctacc cctaagccat    5720
tattactttt ttttttttttt tgagacagag ttttgctctt gttgcccagg ctgcagtgca    5780
gtggtgcaat cttggctcac tgcaacctct gcctcttggg ttcaagcgat tgtcatgcct    5840
tagccttcca gtagctggg attacaggtg tgtgccacta cacctggcta agtagagatg    5900
gggtttcgcc atgttggcca ggctggtctt gaactcctga cctcaagtga tccacctgcc    5960
tccgcctccc aaagtgctgg gattacaggc atgaaccact gcacctggcc tgttacctct    6020
ttcctacaat tttgctcaag tctcccaact ggtcttctgg attcctctct tctgcggtcc    6080
tgttcaaagc ttaagtcaga cagtgtcact tcactcgtct gttttaaaacc tttcaatggc    6140
ccccatttca cgtagaccaa agtccaacgt atttacctgg cctactgatc ttgctcctag    6200
ctacctctga cctcatctcc tgtcaatttc cctctcattc tgttccacca tcctgactgc    6260
cttgacttcc tcaacagaac aagcctgctc ctgcctcagg gcctctgtcc ttattcttcc    6320
tcttcccagg ggtgtgctgg taaaatattt aacaaatagt tctccgggac gggggagaaa    6380
accctcattt gtagcatttg caggtatcta tgtgtaaata ctctcatcaa ggctatttt    6440
gagccactaa tttgccttca ctgaatacag agtttgggaa gagatgcatg ccatcagaac    6500
```

-continued

```
aaatgcaagc cagcaccagc acaccactgc ctcttcctgc aactcttgtc catacacaac    6560
ctcatggctg gctggctcac ttcctgcagg tctctcctca aatatcatct gatgagagac    6620
acattccctg actatgcttt ctaaaatagg ccatatgccc ccacattcat accccatctg    6680
ctgtcattct ttattctttt tataagtgca ttattttcat agcacttatc actacctgtt    6740
gtatattaat caatgatctt ttcccattag aatgtaagtt tcatgaacag gtacttgttt    6800
taatactgta tctccagtcc taatgtgtaa caggagccca ataaatgttt gctttcaaat    6860
ggagaggtta agtaacctgc tcaaatcaca cagctattaa gtggcagaac aggttttcaa    6920
gcaatgcatc tggtggtttt aactaagtcg agatagtttt tattcctaat gcctaaatca    6980
gggcctaggt agtgagctgt gggcacatat taagtattgg ttaaactaaa aataataagc    7040
aaaatggaca ttatctataa aagctttgt ggaaatggct agagctaggg taaggaaaca     7100
aatttggttc cccatacctg cccttcaaga aaataaagct gtcaaggaaa attgggctaa    7160
gagtaggata tgagggatga tggataaggc atgagacatg agaaataag gggattaaa      7220
```

<210> SEQ ID NO 2
<211> LENGTH: 923
<212> TYPE: PRT
<213> ORGANISM: Homo sapiens

<400> SEQUENCE: 2

```
Met Leu Arg Arg Gly Ser Gln Ala Leu Arg Arg Phe Ser Thr Gly Arg
 1               5                  10                  15

Val Tyr Phe Lys Asn Lys Leu Lys Leu Ala Leu Ile Gly Gln Ser Leu
            20                  25                  30

Phe Gly Gln Glu Val Tyr Ser His Leu Arg Lys Glu Gly His Arg Val
        35                  40                  45

Val Gly Val Phe Thr Val Pro Asp Lys Asp Gly Lys Ala Asp Pro Leu
    50                  55                  60

Ala Leu Ala Ala Glu Lys Asp Gly Thr Pro Val Phe Lys Leu Pro Lys
65                  70                  75                  80

Trp Arg Val Lys Gly Lys Thr Ile Lys Glu Val Ala Glu Ala Tyr Arg
                85                  90                  95

Ser Val Gly Ala Glu Leu Asn Val Leu Pro Phe Cys Thr Gln Phe Ile
            100                 105                 110

Pro Met Asp Ile Ile Asp Ser Pro Lys His Gly Ser Ile Ile Tyr His
        115                 120                 125

Pro Ser Ile Leu Pro Arg His Arg Gly Ala Ser Ala Ile Asn Trp Thr
    130                 135                 140

Leu Ile Met Gly Asp Lys Lys Ala Gly Phe Ser Val Phe Trp Ala Asp
145                 150                 155                 160

Asp Gly Leu Asp Thr Gly Pro Ile Leu Leu Gln Arg Ser Cys Asp Val
                165                 170                 175

Glu Pro Asn Asp Thr Val Asp Ala Leu Tyr Asn Arg Phe Leu Phe Pro
            180                 185                 190

Glu Gly Ile Lys Ala Met Val Glu Ala Val Gln Leu Ile Ala Asp Gly
        195                 200                 205

Lys Ala Pro Arg Ile Pro Gln Pro Glu Glu Gly Ala Thr Tyr Glu Gly
    210                 215                 220

Ile Gln Lys Lys Glu Asn Ala Glu Ile Ser Trp Asp Gln Ser Ala Glu
225                 230                 235                 240

Val Leu His Asn Trp Ile Arg Gly His Asp Lys Val Pro Gly Ala Trp
                245                 250                 255
```

-continued

```
Thr Glu Ile Asn Gly Gln Met Val Thr Phe Tyr Gly Ser Thr Leu Leu
            260                 265                 270
Asn Ser Ser Val Pro Pro Gly Glu Pro Leu Glu Ile Lys Gly Ala Lys
        275                 280                 285
Lys Pro Gly Leu Val Thr Lys Asn Gly Leu Val Leu Phe Gly Asn Asp
    290                 295                 300
Gly Lys Ala Leu Thr Val Arg Asn Leu Gln Phe Glu Asp Gly Lys Met
305                 310                 315                 320
Ile Pro Ala Ser Gln Tyr Phe Ser Thr Gly Glu Thr Ser Val Val Glu
                325                 330                 335
Leu Thr Ala Glu Glu Val Lys Val Ala Glu Thr Ile Lys Val Ile Trp
            340                 345                 350
Ala Gly Ile Leu Ser Asn Val Pro Ile Ile Glu Asp Ser Thr Asp Phe
        355                 360                 365
Phe Lys Ser Gly Ala Ser Ser Met Asp Val Ala Arg Leu Val Glu Glu
    370                 375                 380
Ile Arg Gln Lys Cys Gly Gly Leu Gln Leu Gln Asn Glu Asp Val Tyr
385                 390                 395                 400
Met Ala Thr Lys Phe Glu Gly Phe Ile Gln Lys Val Val Arg Lys Leu
                405                 410                 415
Arg Gly Glu Asp Gln Glu Val Glu Leu Val Val Asp Tyr Ile Ser Lys
            420                 425                 430
Glu Val Asn Glu Ile Met Val Lys Met Pro Tyr Gln Cys Phe Ile Asn
        435                 440                 445
Gly Gln Phe Thr Asp Ala Asp Asp Gly Lys Thr Tyr Asp Thr Ile Asn
    450                 455                 460
Pro Thr Asp Gly Ser Thr Ile Cys Lys Val Ser Tyr Ala Ser Leu Ala
465                 470                 475                 480
Asp Val Asp Lys Ala Val Ala Ala Lys Asp Ala Phe Glu Asn Gly
                485                 490                 495
Glu Trp Gly Arg Met Asn Ala Arg Glu Arg Gly Arg Leu Met Tyr Arg
            500                 505                 510
Leu Ala Asp Leu Leu Glu Glu Asn Gln Glu Glu Leu Ala Thr Ile Glu
        515                 520                 525
Ala Leu Asp Ser Gly Ala Val Tyr Thr Leu Ala Leu Lys Thr His Ile
    530                 535                 540
Gly Met Ser Val Gln Thr Phe Arg Tyr Phe Ala Gly Trp Cys Asp Lys
545                 550                 555                 560
Ile Gln Gly Ser Thr Ile Pro Ile Asn Gln Ala Arg Pro Asn Arg Asn
                565                 570                 575
Leu Thr Phe Thr Lys Lys Glu Pro Leu Gly Val Cys Ala Ile Ile Ile
            580                 585                 590
Pro Trp Asn Tyr Pro Leu Met Met Leu Ala Trp Lys Ser Ala Ala Cys
        595                 600                 605
Leu Ala Ala Gly Asn Thr Leu Val Leu Lys Pro Ala Gln Val Thr Pro
    610                 615                 620
Leu Thr Ala Leu Lys Phe Ala Glu Leu Ser Val Lys Ala Gly Phe Pro
625                 630                 635                 640
Lys Gly Val Ile Asn Ile Ile Pro Gly Ser Gly Ile Ala Gly Gln
                645                 650                 655
Arg Leu Ser Glu His Pro Asp Ile Arg Lys Leu Gly Phe Thr Gly Ser
            660                 665                 670
```

-continued

```
Thr Pro Ile Gly Lys Gln Ile Met Lys Ser Cys Ala Val Ser Asn Leu
            675                 680                 685
Lys Lys Val Ser Leu Glu Leu Gly Gly Lys Ser Pro Leu Ile Ile Phe
        690                 695                 700
Asn Asp Cys Glu Leu Asp Lys Ala Val Arg Met Gly Met Gly Ala Val
705                 710                 715                 720
Phe Phe Asn Lys Gly Glu Asn Cys Ile Ala Ala Gly Arg Leu Phe Val
                725                 730                 735
Glu Glu Ser Ile His Asp Glu Phe Val Thr Arg Val Val Glu Glu Ile
            740                 745                 750
Lys Lys Met Lys Ile Gly Asp Pro Leu Asp Arg Ser Thr Asp His Gly
        755                 760                 765
Pro Gln Asn His Lys Ala His Leu Glu Lys Leu Leu Gln Tyr Cys Glu
    770                 775                 780
Thr Gly Val Lys Glu Gly Ala Thr Leu Val Tyr Gly Gly Arg Gln Val
785                 790                 795                 800
Gln Arg Pro Gly Phe Phe Met Glu Pro Thr Val Phe Thr Asp Val Glu
                805                 810                 815
Asp Tyr Met Tyr Leu Ala Lys Glu Glu Ser Phe Gly Pro Ile Met Val
            820                 825                 830
Ile Ser Lys Phe Gln Asn Gly Asp Ile Asp Gly Val Leu Gln Arg Ala
        835                 840                 845
Asn Ser Thr Glu Tyr Gly Leu Ala Ser Gly Val Phe Thr Arg Asp Ile
    850                 855                 860
Asn Lys Ala Met Tyr Val Ser Glu Lys Leu Glu Ala Gly Thr Val Phe
865                 870                 875                 880
Ile Asn Thr Tyr Asn Lys Thr Asp Val Ala Ala Pro Phe Gly Gly Val
                885                 890                 895
Lys Gln Ser Gly Phe Gly Lys Asp Leu Gly Glu Glu Ala Leu Asn Glu
            900                 905                 910
Tyr Leu Lys Thr Lys Thr Val Thr Leu Glu Tyr
        915                 920
```

<210> SEQ ID NO 3
<211> LENGTH: 2772
<212> TYPE: DNA
<213> ORGANISM: Homo sapiens
<220> FEATURE:
<221> NAME/KEY: CDS
<222> LOCATION: (1)...(2772)

<400> SEQUENCE: 3

```
atg ctg cgg cgg ggc agc cag gcg ctc cgg cgc ttc tcc act ggc cgg     48
Met Leu Arg Arg Gly Ser Gln Ala Leu Arg Arg Phe Ser Thr Gly Arg
 1               5                  10                  15 gtt tat ttc aaa aac aag ctg aag ttg gca cta att ggc cag agc ctc     96
Val Tyr Phe Lys Asn Lys Leu Lys Leu Ala Leu Ile Gly Gln Ser Leu
             20                  25                  30 ttt gga caa gaa gtc tat agc cac ctc cgc aaa gag ggc cac cga gta    144
Phe Gly Gln Glu Val Tyr Ser His Leu Arg Lys Glu Gly His Arg Val
         35                  40                  45 gta ggg gtg ttc aca gtt cca gac aag gat gga aaa gct gac cct ctg    192
Val Gly Val Phe Thr Val Pro Asp Lys Asp Gly Lys Ala Asp Pro Leu
     50                  55                  60 gct ttg gct gca gag aaa gat ggg acc cct gtg ttc aag ctt cct aaa    240
Ala Leu Ala Ala Glu Lys Asp Gly Thr Pro Val Phe Lys Leu Pro Lys
 65                  70                  75                  80
```

```
tgg agg gtc aag ggc aag acc atc aaa gaa gtg gca gaa gcc tac aga      288
Trp Arg Val Lys Gly Lys Thr Ile Lys Glu Val Ala Glu Ala Tyr Arg
                85                  90                  95 tcc gtg ggt gca gag cta aat gtg ctc cct ttc tgc act cag ttc att      336
Ser Val Gly Ala Glu Leu Asn Val Leu Pro Phe Cys Thr Gln Phe Ile
            100                 105                 110 ccc atg gat ata att gat agt cca aag cac ggc tct atc att tat cac      384
Pro Met Asp Ile Ile Asp Ser Pro Lys His Gly Ser Ile Ile Tyr His
        115                 120                 125 cca tcc atc ctg ccc agg cac aga gga gcc tct gct atc aat tgg act      432
Pro Ser Ile Leu Pro Arg His Arg Gly Ala Ser Ala Ile Asn Trp Thr
    130                 135                 140 cta att atg gga gat aag aaa gct ggg ttt tct gtt ttc tgg gct gat      480
Leu Ile Met Gly Asp Lys Lys Ala Gly Phe Ser Val Phe Trp Ala Asp
145                 150                 155                 160 gat ggc ttg gat aca gga ccc atc ctt ctt cag aga tca tgt gat gtt      528
Asp Gly Leu Asp Thr Gly Pro Ile Leu Leu Gln Arg Ser Cys Asp Val
                165                 170                 175 gaa ccc aat gat aca gtg gat gca ctt tat aat cgg ttt ctt ttt cct      576
Glu Pro Asn Asp Thr Val Asp Ala Leu Tyr Asn Arg Phe Leu Phe Pro
            180                 185                 190 gaa gga atc aag gcc atg gta gaa gct gtc caa ctc ata gct gat gga      624
Glu Gly Ile Lys Ala Met Val Glu Ala Val Gln Leu Ile Ala Asp Gly
        195                 200                 205 aaa gct cct cgt ata ccc cag cca gaa gaa ggg gca aca tat gaa ggt      672
Lys Ala Pro Arg Ile Pro Gln Pro Glu Glu Gly Ala Thr Tyr Glu Gly
    210                 215                 220 atc cag aaa aag gaa aat gct gag att tct tgg gac cag tct gcc gaa      720
Ile Gln Lys Lys Glu Asn Ala Glu Ile Ser Trp Asp Gln Ser Ala Glu
225                 230                 235                 240 gtt tta cat aac tgg att cga ggt cat gat aaa gtc cct gga gct tgg      768
Val Leu His Asn Trp Ile Arg Gly His Asp Lys Val Pro Gly Ala Trp
                245                 250                 255 aca gag ata aat gga cag atg gtc act ttc tat ggc tcg aca tta ctg      816
Thr Glu Ile Asn Gly Gln Met Val Thr Phe Tyr Gly Ser Thr Leu Leu
            260                 265                 270 aat agc tct gtg cct cct gga gaa cca ctg gaa att aaa ggt gcc aag      864
Asn Ser Ser Val Pro Pro Gly Glu Pro Leu Glu Ile Lys Gly Ala Lys
        275                 280                 285 aag cct ggt ctc gtt acc aaa aat gga ctt gtt ctt ttt ggt aac gat      912
Lys Pro Gly Leu Val Thr Lys Asn Gly Leu Val Leu Phe Gly Asn Asp
    290                 295                 300 gga aaa gca ctg acg gtg aga aat ctg cag ttt gaa gat gga aaa atg      960
Gly Lys Ala Leu Thr Val Arg Asn Leu Gln Phe Glu Asp Gly Lys Met
305                 310                 315                 320 atc cct gcc tct cag tac ttt tca acg ggt gag acg tca gtg gta gaa     1008
Ile Pro Ala Ser Gln Tyr Phe Ser Thr Gly Glu Thr Ser Val Val Glu
                325                 330                 335 ctg aca gct gaa gag gtg aaa gtg gca gag acc atc aag gtc atc tgg     1056
Leu Thr Ala Glu Glu Val Lys Val Ala Glu Thr Ile Lys Val Ile Trp
            340                 345                 350 gct gga att tta agc aat gtc ccc att att gaa gac tca aca gac ttc     1104
Ala Gly Ile Leu Ser Asn Val Pro Ile Ile Glu Asp Ser Thr Asp Phe
        355                 360                 365 ttt aaa tct gga gca agc tca atg gat gtt gcc agg ctg gtt gaa gag     1152
Phe Lys Ser Gly Ala Ser Ser Met Asp Val Ala Arg Leu Val Glu Glu
    370                 375                 380 atc aga cag aaa tgt ggt ggg ctt cag ttg cag aat gaa gat gtc tat     1200
Ile Arg Gln Lys Cys Gly Gly Leu Gln Leu Gln Asn Glu Asp Val Tyr
385                 390                 395                 400
```

```
atg gcc acc aag ttt gaa ggc ttt atc caa aag gtc gtg agg aaa ctg      1248
Met Ala Thr Lys Phe Glu Gly Phe Ile Gln Lys Val Val Arg Lys Leu
            405                 410                 415 aga gga gaa gat caa gag gtg gag ctg gtt gta gat tat att tca aag      1296
Arg Gly Glu Asp Gln Glu Val Glu Leu Val Val Asp Tyr Ile Ser Lys
                420                 425                 430 gag gtc aat gaa atc atg gta aaa atg cca tac cag tgt ttc ata aat      1344
Glu Val Asn Glu Ile Met Val Lys Met Pro Tyr Gln Cys Phe Ile Asn
            435                 440                 445 gga cag ttc aca gat gca gac gat gga aag act tac gac act atc aac      1392
Gly Gln Phe Thr Asp Ala Asp Asp Gly Lys Thr Tyr Asp Thr Ile Asn
        450                 455                 460 cca aca gat gga tct aca ata tgc aaa gta tcc tac gct tct ttg gcg      1440
Pro Thr Asp Gly Ser Thr Ile Cys Lys Val Ser Tyr Ala Ser Leu Ala
465                 470                 475                 480 gat gtt gat aaa gca gta gca gca gca aaa gat gct ttt gaa aac ggt      1488
Asp Val Asp Lys Ala Val Ala Ala Ala Lys Asp Ala Phe Glu Asn Gly
                485                 490                 495 gaa tgg gga aga atg aat gca aga gaa aga gga aga ttg atg tat aga      1536
Glu Trp Gly Arg Met Asn Ala Arg Glu Arg Gly Arg Leu Met Tyr Arg
            500                 505                 510 ctt gca gac cta ctg gaa gag aac caa gaa gag ctg gca act att gaa      1584
Leu Ala Asp Leu Leu Glu Glu Asn Gln Glu Glu Leu Ala Thr Ile Glu
        515                 520                 525 gcc ctt gat tca ggg gct gtc tat acc ttg gcc ctg aag aca cac att      1632
Ala Leu Asp Ser Gly Ala Val Tyr Thr Leu Ala Leu Lys Thr His Ile
    530                 535                 540 gga atg tct gtg caa aca ttc aga tat ttt gct ggc tgg tgc gac aaa      1680
Gly Met Ser Val Gln Thr Phe Arg Tyr Phe Ala Gly Trp Cys Asp Lys
545                 550                 555                 560 att cag ggt tct act att cca atc aac cag gcc cgt cca aat cgc aat      1728
Ile Gln Gly Ser Thr Ile Pro Ile Asn Gln Ala Arg Pro Asn Arg Asn
                565                 570                 575 ctg acc ttc acc aag aaa gag cca ctc ggt gtc tgt gcc att att att      1776
Leu Thr Phe Thr Lys Lys Glu Pro Leu Gly Val Cys Ala Ile Ile Ile
            580                 585                 590 ccc tgg aac tac ccg ctg atg atg ctg gca tgg aag agt gct gcg tgt      1824
Pro Trp Asn Tyr Pro Leu Met Met Leu Ala Trp Lys Ser Ala Ala Cys
        595                 600                 605 ttg gca gca ggc aat acc tta gtg ctc aag cca gca cag gtc acg ccc      1872
Leu Ala Ala Gly Asn Thr Leu Val Leu Lys Pro Ala Gln Val Thr Pro
    610                 615                 620 ttg act gct ttg aag ttt gca gaa ctg tct gtg aaa gca ggt ttt cca      1920
Leu Thr Ala Leu Lys Phe Ala Glu Leu Ser Val Lys Ala Gly Phe Pro
625                 630                 635                 640 aag ggg gtc atc aac atc att cca ggc tca ggt ggc ata gca gga caa      1968
Lys Gly Val Ile Asn Ile Ile Pro Gly Ser Gly Gly Ile Ala Gly Gln
                645                 650                 655 cgt ctg tct gaa cat cct gac atc cgc aaa ctt ggt ttc act gga tcc      2016
Arg Leu Ser Glu His Pro Asp Ile Arg Lys Leu Gly Phe Thr Gly Ser
            660                 665                 670 act cct att ggc aaa cag atc atg aag agc tgt gct gtt agc aac ttg      2064
Thr Pro Ile Gly Lys Gln Ile Met Lys Ser Cys Ala Val Ser Asn Leu
        675                 680                 685 aag aaa gtt tcc ctt gag ctt ggt ggc aag tct cca ctt ata ata ttt      2112
Lys Lys Val Ser Leu Glu Leu Gly Gly Lys Ser Pro Leu Ile Ile Phe
    690                 695                 700 aat gac tgt gaa ctt gac aag gct gtg cga atg ggc atg gga gca gta      2160
Asn Asp Cys Glu Leu Asp Lys Ala Val Arg Met Gly Met Gly Ala Val
```

```
705                     710                     715                     720
ttt ttc aac aaa gga gag aac tgt att gct gct ggg cgg ttg ttc gtg              2208
Phe Phe Asn Lys Gly Glu Asn Cys Ile Ala Ala Gly Arg Leu Phe Val
                725                     730                     735 gaa gaa tcc atc cac gac gaa ttt gtg aca aga gtg gta gaa gaa att              2256
Glu Glu Ser Ile His Asp Glu Phe Val Thr Arg Val Val Glu Glu Ile
                740                     745                     750 aaa aag atg aaa att ggt gat cca ctt gac aga tcc act gat cat ggg              2304
Lys Lys Met Lys Ile Gly Asp Pro Leu Asp Arg Ser Thr Asp His Gly
            755                     760                     765 ccc caa aat cat aag gct cat ctg gaa aag ctg ctg caa tac tgt gaa              2352
Pro Gln Asn His Lys Ala His Leu Glu Lys Leu Leu Gln Tyr Cys Glu
        770                     775                     780 act gga gtg aaa gaa ggg gcc act ttg gtg tac ggg gga aga caa gtc              2400
Thr Gly Val Lys Glu Gly Ala Thr Leu Val Tyr Gly Gly Arg Gln Val
785                     790                     795                     800 caa agg cca ggc ttt ttc atg gag ccg acc gtg ttc aca gat gtg gaa              2448
Gln Arg Pro Gly Phe Phe Met Glu Pro Thr Val Phe Thr Asp Val Glu
                805                     810                     815 gac tac atg tac ctc gcc aaa gag gaa tcc ttt ggg cct att atg gtc              2496
Asp Tyr Met Tyr Leu Ala Lys Glu Glu Ser Phe Gly Pro Ile Met Val
                820                     825                     830 att tct aaa ttc caa aat ggg gac atc gat gga gtg ttg cag cga gca              2544
Ile Ser Lys Phe Gln Asn Gly Asp Ile Asp Gly Val Leu Gln Arg Ala
            835                     840                     845 aat agt aca gag tat ggt ttg gcc tca ggg gtt ttt aca aga gac ata              2592
Asn Ser Thr Glu Tyr Gly Leu Ala Ser Gly Val Phe Thr Arg Asp Ile
        850                     855                     860 aac aaa gct atg tat gtg agt gaa aaa ctg gaa gca gga act gtt ttt              2640
Asn Lys Ala Met Tyr Val Ser Glu Lys Leu Glu Ala Gly Thr Val Phe
865                     870                     875                     880 att aac aca tac aac aag aca gat gtg gcg gcc cca ttt ggc gga gtt              2688
Ile Asn Thr Tyr Asn Lys Thr Asp Val Ala Ala Pro Phe Gly Gly Val
                885                     890                     895 aaa caa tct ggc ttt gga aaa gac tta ggt gag gaa gct cta aat gaa              2736
Lys Gln Ser Gly Phe Gly Lys Asp Leu Gly Glu Glu Ala Leu Asn Glu
            900                     905                     910 tat ctc aaa acc aag acg gtg aca ctg gaa tat tag                              2772
Tyr Leu Lys Thr Lys Thr Val Thr Leu Glu Tyr  *
        915                     920

<210> SEQ ID NO 4
<211> LENGTH: 492
<212> TYPE: PRT
<213> ORGANISM: Artificial Sequence
<220> FEATURE:
<223> OTHER INFORMATION: Aldehyde dehydrogenase Pfam consensus sequence

<400> SEQUENCE: 4

Glu Trp Val Asp Ser Ala Ser Gly Lys Thr Phe Glu Val Val Asn Pro
1               5                   10                  15

Ala Asn Lys Gly Glu Val Ile Gly Arg Val Pro Glu Ala Thr Ala Glu
            20                  25                  30

Asp Val Asp Ala Ala Val Lys Ala Ala Lys Glu Ala Phe Lys Ser Gly
        35                  40                  45

Pro Trp Trp Ala Lys Val Pro Ala Ser Glu Arg Ala Arg Ile Leu Arg
    50                  55                  60

Lys Leu Ala Asp Leu Ile Glu Glu Arg Glu Asp Glu Leu Ala Ala Leu
65                  70                  75                  80
```

-continued

```
Glu Thr Leu Asp Leu Gly Lys Pro Leu Ala Glu Ala Lys Gly Asp Thr
                 85                  90                  95

Glu Val Gly Arg Ala Ile Asp Glu Ile Arg Tyr Tyr Ala Gly Trp Ala
            100                 105                 110

Arg Lys Leu Met Gly Glu Arg Val Ile Pro Ser Leu Ala Thr Asp
            115                 120                 125

Gly Asp Glu Glu Leu Asn Tyr Thr Arg Arg Glu Pro Leu Gly Val Val
130                 135                 140

Gly Val Ile Ser Pro Trp Asn Phe Pro Leu Leu Ala Leu Trp Lys
145                 150                 155                 160

Leu Ala Pro Ala Leu Ala Ala Gly Asn Thr Val Val Leu Lys Pro Ser
                165                 170                 175

Glu Gln Thr Pro Leu Thr Ala Leu Leu Leu Ala Glu Leu Ile Glu Glu
                180                 185                 190

Ala Gly Ala Asn Asn Leu Pro Lys Gly Val Val Asn Val Val Pro Gly
                195                 200                 205

Phe Gly Ala Glu Val Gly Gln Ala Leu Leu Ser His Pro Asp Ile Asp
            210                 215                 220

Lys Ile Ser Phe Thr Gly Ser Thr Glu Val Gly Lys Leu Ile Met Glu
225                 230                 235                 240

Ala Ala Ala Ala Lys Asn Leu Lys Lys Val Thr Leu Glu Leu Gly Gly
                245                 250                 255

Lys Ser Pro Val Ile Val Phe Asp Asp Ala Asp Leu Asp Lys Ala Val
                260                 265                 270

Glu Arg Ile Val Phe Gly Ala Phe Gly Asn Ala Gly Gln Val Cys Ile
            275                 280                 285

Ala Pro Ser Arg Leu Leu Val His Glu Ser Ile Tyr Asp Glu Phe Val
290                 295                 300

Glu Lys Leu Lys Glu Arg Val Lys Lys Leu Lys Leu Ile Gly Asp Pro
305                 310                 315                 320

Leu Asp Ser Asp Thr Asn Ile Tyr Gly Pro Leu Ile Ser Glu Gln Gln
                325                 330                 335

Phe Asp Arg Val Leu Ser Tyr Ile Glu Asp Gly Lys Glu Glu Gly Ala
            340                 345                 350

Lys Val Leu Cys Gly Gly Glu Arg Asp Glu Ser Lys Glu Tyr Leu Gly
            355                 360                 365

Gly Gly Tyr Tyr Val Gln Pro Thr Ile Phe Thr Asp Val Thr Pro Asp
370                 375                 380

Met Lys Ile Met Lys Glu Glu Ile Phe Gly Pro Val Leu Pro Ile Ile
385                 390                 395                 400

Lys Phe Lys Asp Leu Asp Glu Ala Ile Glu Leu Ala Asn Asp Thr Glu
                405                 410                 415

Tyr Gly Leu Ala Ala Tyr Val Phe Thr Lys Asp Ile Leu Ala Arg Ala
            420                 425                 430

Phe Arg Val Ala Lys Ala Leu Glu Ala Gly Ile Val Trp Val Asn Asp
            435                 440                 445

Val Cys Val His Ala Ala Glu Pro Gln Leu Pro Phe Gly Gly Val Lys
        450                 455                 460

Gln Ser Ser Gly Ile Gly Arg Glu His Gly Gly Lys Tyr Gly Leu Glu
465                 470                 475                 480

Glu Tyr Thr Glu Ile Lys Thr Val Thr Ile Arg Leu
                485                 490
```

What is claimed is:

1. An isolated nucleic acid molecule selected from the group consisting of:
   a) the nucleotide sequence set forth in SEQ ID NO:1;
   b) the nucleotide sequence set forth in SEQ ID NO:3;
   c) the nucleotide sequence of the cDNA insert of the plasmid deposited with ATCC as Patent Deposit No. PTA-3424;
   d) a nucleotide sequence having at least 97% sequence identity with the nucicotide sequence set forth in SEQ ID NO:1 wherein said nucleotide sequence having at least 97% sequence identity with the nucleotide sequence set forth in SEQ ID NO:1 encodes a polypeptide having aldehyde dehydrogenase activity;
   e) a nucleotide sequence having at least 97% sequence identity with the nucleotide sequence set forth in SEQ ID NO:3 wherein said nucleotide sequence having at least 97% sequence identity with the nucleotide sequence set forth in SEQ ID NO:3 encodes a polypeptide having aidehyde dehydrogenase activity;
   f) a nucleotide sequence having at least 97% sequence identity with the cDNA insert of the plasraid deposited with ATCC as Patent Deposit No. PTA-3424 wherein said nucleotide sequence encodes a polypeptide having aldehyde dehydrogenase activity;
   g) the nucleotide sequence of a fragment of the nucleotide sequence set forth in SEQ ID NO:1, wherein said fragnieiit comprises at least 300 contiguous nucleotides of the nucleotide sequence set forth in SEQ ID NO:1 and encodes a polypeptide having aldehyde dehydrogenase activity;
   h) the nucleotide sequence of a fagment of the nucleotide sequence set forth in SEQ ID NO:3, wherein said fragment comprises at least 300 contiguous nucleotides of the nucleotide sequence set forth in SEQ ID NO:3 and encodes a polypeptide having aldehyde dehydrogenase activity;
   i) the nucleotide sequence of a fragment of the cDNA insert of the plasmid deposited with ATCC as Patent Deposit No. PTA-3424, wherein said fragment comprises at least 300 contiguous nucleotides of the cDNA insert of the plusmid deposited with ATCC as Patent Deposit No. PTA-3424 and encodes a polypeptide having aidehyde dehydrogenase activity;
   j) a nucleotide sequence encoding the amino acid sequence set forth in SEQ ID NO:2;
   k) a nucleotide sequence encoding the amino acid sequence encoded by the cDNA insert of the plasmid deposited with ATCC as Patent Deposit No. PTA-3424,
   l) a nucleotide sequence encoding a fragment of the amino acid sequence set forth in SEQ TD NO:2, wherein the fragment comprises at least 50 contiguous amilo acids of SEQ ID NO:2 and the fragment has aldchyde dehydrogenase activity;
   m) a nucleotide sequence encoding a fragment of the amino acid sequence encoded by the eDNA insert of the plasmid deposited with ATCC as Patent Deposit No. PTA-3424, wherein the fragment comprises at least 50 contiguous amino acids of the amino acid sequence encoded by the cDNA insert of the plasmid deposited with ATCC as Patent Deposit No. PTA-3424 and the fragment has aldehyde dehydrogenase activity; and
   n) a nucleotide sequence completely complementary to at least one nucleotide sequence of a), b), c), d), e), f), g), h), i), j), k), l), or m).

2. The isolated nucleic acid molecule of claim 1, wherein said nucleic acid molecule comprises a nucleotide sequence selected fToni the group consisting of:
   a) a nucleotide sequence having at least 98% sequence identity with the nucleotide sequence set forth in SEQ ID NO;1 wherein said nucleotide sequence having at least 98% sequence identity with the nucleotide sequence set forli in SEQ ID NO:1 encodes a polypeptide having aldehyde dehydrogenase activity;
   b) a nucleetide sequence having at least 98% sequence identity with the nucleotide sequence set forth in SEQ ID NO:3 wherein said nucleotide sequence having at least 98% sequence identity with the nucleotide sequence set forth in SEQ ID NO:3 encodes a polypoptide having aldehyde dehydrogenase activity;
   c) a nutleotide sequence having at least 98% sequence identity with the cDNA insert of the plasmid deposited with ATCC as Patent Deposit No. PTA-3424 wherein said nucleotidc sequence encodes a polypepticle having aldlehydc dehydrogenase activity; and
   d) a nucleotide sequence completely complementary to at least one nucleotide sequence of a), b), or c).

3. The isolated nucleic acid molecule of claim 2, wherein said nucleic acid molecule comprises a nucleotide sequence selectod from the group consisting of:
   a) the nucleotide sequence set forth in SEQ ID NO:1;
   b) the nucleotide sequence set forth in SEQ ID NO:3;
   c) the nucleotide sequence of the cDNA insert of the plasmid deposited with ATCC as Patent Deposit No. PTA-3424;
   d) a nucleotide sequence encoding the amino acid sequence set forth in SEQ ID NO:2; and
   e) a nucleotide sequence completely complementary to at least one nucleotide sequence of a), b), c), or d).

4. The isolated nucleic acid moleculc of claim 2, wherein said nucleic acid molecule comprises the nucleotide sequence set forth in SEQ ID NO:1 or a completecomplement thereof.

5. The isolated nucleic acid molecule of claim 3, wherein said nucleic acid molecule comprises either strand of the cDNA insert of the plasmid deposited with ATCC as Patent Deposit No. PTA-3424.

6. The nucleic acid molecule of claim 1 wherein said nucleic acid molecule further comprises vector nucleic acid sequences.

7. The nucleic acid molecule of claim 1 wherein said nucleic acid molecule further comprises a nucleotide sequence encoding at least one heterologous polypeptide.

8. A host cell which contains the nucleic acid molecules of claim 6.

9. The host cell of claim 8 wherein said host cell is a non-human mammalian host cell.

10. A non-human mammalian host cell containing the nucleic acid molecule of claim 1.

11. The nucleic acid molecule of claim 3 wherein said nucleic acid molecule further comprises vector nucleic acid sequences.

12. The nucleic acid molecule of claim 3 wherein said nucleic acid molecule further comprises a nucleotide sequence encoding at least one heterologous polypeptide.

13. A host cell which contains the nucleic acid molecules of claim 12.

14. The host cell of claim 13 wherein said host cell is a non-human mammalian host cell.

15. A non-human mammalian host cell containing the nucleic acid molecule of claim 3.

16. A method for producing an aldehde dehydrogenase acid sequence selected from the group consisting of:
  a) the amino acid sequence set forth in SEQ ID NO:2,
  b) the amino acid sequence encoded by the cDNA insert of the plasmid deposited with ATCC as Patent Deposit No. PTA-3424;
  c) the amino acid sequence of a fragment of the amino acid sequence set forth in SEQ ID NO:2 wherein the fragment comprises at least 50 contiguous amino acids of SEQ ID NO:2 and the fragment has aldehyde dehydrogenase activity;
  d) the amino acid sequence of the amino acid sequence encoded by the cDNA insert of the plasmid deposited with ATCC as Patent Deposit No. PTA-3424, wherein the fragment coniprises at least 50 contiguous amino acids of the amino acid sequence encoded by the cDNA insert of the plasmid deposited with the ATCC as Patent Deposit No. PTA-3424 and the fragment has aldehyde dehydrogenase activity;
  e) the amino acid sequence of a sequence variant of the amino acid sequence set forth in SEQ ID NO:2 wherein said sequence variant has aldehyde dehydrngenase activity and is encoded by a nucleotide sequence having at least 98% sequence identity with the nucleotide sequence set forth in SEQ ID NO:3; and
  f) the amino acid sequence of a sequence variant of tie amino acid sequence encoded by the cDNA insert of the plasmid deposited with the ATCC as Patent Deposit No. PTA-3424 wherein said sequence variant has aidehyde dehydrogenase activity and is encoded by a nuclootide sequence having at least 98% sequence identity with the cDNA insert of the plasmid deposited with the ATCC as Patent Deposit No. PTA-3424;
  comprising culturing a host cell containing a nucleic acid molecule encoding said polypeptide under conditions such that said polypeptide is expressed.

17. The method of claim 16, wherein said polypeptide comprises the amino acid sequence set forth in SEQ ID NO:2.

18. The method of claim 16, wherein said polypeptide comprises the amino acid sequence encoded by the cDNA insert of the plasmid deposited with ATCC as Patent Deposit No. PTA-3424.

19. The isolated nucleic acid molecule of claim 1, wherein said nucleic acid molecule comprises a nucleotide sequence encoding a fragment of the amino acid sequence set forth in SEQ ID NO:2, wherein the fragment has aldehyda dehydrogenase activity and comprises at least SO contiguous amino acids of SEQ ID NO:2.

20. The isolated nucleic acid molecule of claim 19, wherein said nucleic acid molecule comprises a nucleotide sequence encoding a fragment of the amino acid sequence set forth in SEQ TD NO:2, wherein the fragment has aldehyde dehydrogenase activity and comprises at least 100 contiguous amino acids of SEQ ID NO:2.

21. The isolated nucleic acid molecule of claim 3, wherein said nucleic acid molecule comprises the nucleotide sequence set forth in SEQ ID NO:1.

22. The isolated nucleic acid molecule of claim 3, wherein said nucleic acid molecule comprises the nucleotide sequence set forth in SEQ ID NO:3.

23. The isolated nucleic acid molecule of claim 3, wherein said nucleic acid molecule comprises a nucleotide sequence encoding the amino acid sequence set forth in SEQ ID NO:2.

24. The method of claim 16, wherein said polypeptide comprises the amino acid sequence of a fragment ofthe amino acid sequence set forth in SEQ ID NO:2, wherein the fragment has aldehyde dehydrogenase activity and comprises at least 100 contiguous amino acids of SEQ ID NO:2.

25. The method of claim 24, wherein said polypeptide comprises the amino acid sequence of a fragment of the amino acid sequence set forth In SEQ ID NO:2, wherein the fragment has aldellyde dehydrogenase activity and comprises at least 200 contiguous amino acids of SEQ ID NO:2.

26. An isolated nucleic acid molecule comprising a nucleotide sequence encoding a fragment of the amino acid sequence set forth in SEQ ID NO:2, wherein the fragment has aldehyde dehydrogenase activity and consists of at least 100 contiguous amino acids of SEQ ID NO:2.

27. The isolated nucleic acid molecule of claim 26, wherein said fragment consists of at least 200 contiguous amino acids of SEQ D NO;2.

28. The isolated nticleic acid molecule of claim 27, wherein said fragment consists oral least 300 contiguous amino acids of SEQ ID NO:2.

29. The isolated nucleic acid molecule of claim 28 wherein said fragment consists of at least 400 contiguous amino acids of SEQ ID NO:2.

30. The isolated nucleic acid molecule of claim 29, wherein said fragment consists of at least 500 contiguous amino acids of SEQ ID NO:2.

31. The isolated nucleic acid molecule of claim 1 wherein said nucleic acid molecule comprises a nucleotide sequence selected from the group consisting of:
  a) a nucleotide sequence having at least 99% sequence identity with the nucleotide sequence set forth in SEQ ID NO:1 wherein said nucleotide sequence having at least 99% sequence identity with the nucleotide sequence set forth in SEQ ID NO:1 encodes a polypeptide having aidehyde dehydrogenase activity;
  b) a nucleotide sequence having at least 99% sequence identity with the nucleotide sequence set forth in SEQ ID NO:3 wherein said nucleotide sequence having at least 99% sequence identity with the nucleotide sequence set forth in SEQ ID NO:3 encodes a polypeptide having aldehyde dehydrogenase activity;
  c) a ntcleotide sequence having at least 99% sequence identity with the cDNA insert of the plasmid deposited with ATCC as Patent Deposit No. PTA-3424 wherein said nucleotide sequence encodes a polypeptide having aldehyde dehydrogenase activity; and
  d) a nucleotide sequence completely complementary to at least one nucleotide sequence of a), b), or c).

* * * * *